United States Patent [19]
Cheng et al.

[11] Patent Number: 5,985,824
[45] Date of Patent: *Nov. 16, 1999

[54] METHODS AND COMPOSITIONS FOR TREATING CYSTIC FIBROSIS

[75] Inventors: Seng Hing Cheng, Wellesley; Canwen Jiang, Marlboro, both of Mass.

[73] Assignee: Genzyme Corporation, Framingham, Mass.

[*] Notice: This patent is subject to a terminal disclaimer.

[21] Appl. No.: 08/956,320

[22] Filed: Oct. 23, 1997

Related U.S. Application Data

[63] Continuation-in-part of application No. 08/807,398, Feb. 27, 1997, Pat. No. 5,834,421.

[51] Int. Cl.$^6$ .............................. A61K 38/00; A01N 37/18
[52] U.S. Cl. .............................. 514/2; 514/540; 514/588; 514/619; 514/851; 560/33; 564/59; 564/160; 564/161; 564/192
[58] Field of Search ................................ 514/2, 540, 588, 514/619, 851; 560/33; 564/59, 160, 161, 192; 424/439; 206/828

[56] References Cited

U.S. PATENT DOCUMENTS

| | | | |
|---|---|---|---|
| 5,637,613 | 6/1997 | Renaut et al. | 514/540 |
| 5,674,898 | 10/1997 | Cheng et al. | 514/557 |

OTHER PUBLICATIONS

Cheng, S.H. et al. Defective intracellular transport and processing of CFTR is the molecular basis of most cyctic fibrosis. *Cell* 63:827–834 (1990).

Jensen, T.J., Loo, M.A., Pind, S., Williams, D.B., Goldberg, A.L., and Riordan, J.R. Multiple proteolytic systems including proteasome, contribute to CFTR processing. *Cell* 83:129–135 (1995).

Ward, C.L., Omura, S., & Kopito, R.R. Degradation of CFTR by the uniquitin–proteasome pathway. *Cell* 83:121–127 (1995).

Denning, G.M., Anderson, M.P., Amara, J.F., Marshall, J., Smith, A.E., and Welsh, M.J. Processing of mutant cystic fibrosis transmembrane conductance regulator is temperature–sensitive. *Nature* 358:761–764 (1992).

Sato, S., Ward, C.L., Krouse, M.E., Wine, J.J., & Kopito, R.R. Glycerol reverses the misfolding phenotype of the most common cystic fibrosis mutation, *J. Biol. Chem.* 271:635–638 (1996).

Cheng, S.H. et al. Functional activation of the cystic fibrosis trafficking mutant κ–CFTR by overexpression. *Am. J. Physiol.* 268L615–L624 (1995).

Hartl, F.U. Molecular changes in cellular protein folding. *Nature* 381:571–580 (1996).

Pind, S., Riordan, J.R., and Williams, D.B. Participation of the endoplasmic reticulum chaperone calnexin (p88, IP90) in the biogenesis of the cystic fibrosis transmembrane conductance regulator. *J.Biol. Chem.* 269:12784–12788 (1994).

Umezawa, H. et al. Structure of antitumor antibiotic, spergualin. *J. Antibiotics* 34:1622–1624 (1981).

Nadler, S.G., Tepper, M.A., Schacter, B., and Mazzucco. Interaction of the immunosuppressant deoxyspergualin with a member of the Hsp70 family of heat shock proteins. *Science* 258:484–486 (1992).

Nadeau, K., Nadler, S.G., Saulnier, M., Tepper, M.A., and Walsh, C.T. Quantitation of the interaction of the immunosuppressant deoxyspergualin and analogs Hsc70 and Hsp90. *Biochemistry* 33:2561–2567.

Marshall, J. et al. Stoichiometry of recombinant cystic fibrosis transmembrane conductance regulator in epithelial cells and its functional reconstitution into cells in vitro. *J. Biol. Chem.* 269:2987–2995 (1994).

Jefferson, D.M. et al. Expression of normal and cystic fibrosis phenotypes by continuous airway epithelial cell lines. *Am. J. Physiol.* 259:L496–L505 (1990).

Tepper, M.A., Nadler, S.G., Esselstyn, J.M., and Sterbenz, K.G. Deoxyspergualin inhibits κ light chain expression in 70Z/3 pre–B cells by blocking lipopolysaccharide–induced NF–κB activation. *J. Immunol.* 155:2427–2436 (1995).

Yankaskas, J.R. et al. Papilloma virus immortalized tracheal epithelial cells retain a well–differentiated phenotype.*Am. J. Physiol.* 264:C1219–C1230 (1993).

Grubman, S.A. et al. Correction of the cystic fibrosis defect by gene complementation in human intrahepatic bilary epithelial cell lines. *Gastroenterology* 108:584–592 (1995).

Dalemans, W. et al. Altered chloride ion channel kinetics associated with ΔF508 cystic fibrosis mutation. *Nature* 354:526–528 (1991).

Howard, M., Frizzell, R.A., and Bedwell, D.M. Aminoglycoside antibiotics restore CFTR function by overcoming premature stop mutations. *Nature Genetics* 2:467–469 (1996).

Rubenstein, R.C., Brusilow, S.W., Hamosh, A., and Zeitlin, P.L. Clinical trials of 4–phenylbutyrate for correction of sweat duct abnormalities in ΔF508 homozygous cystic fibrosis patients. *Pediat. Pulmonology* 13:259 (1996).

Nossner, E., Goldberg, J.E., Naftzger, C., Lyu, S.C., Clayberger, C., and Krensky, A.M. HLA–derived peptides which inhibit T cell function bind to members of the heat–shock protein 70 family. *J. Exp. Med.* 183:339–348 (1996).

Yang, I.C.H., Cheng, T.H., Wang, F., Price, E.M., and Hwang, T.C. Modulation of CFTR chloride channels by calyculin A and genistein. *Am. J. Physiol.* 272:C142–C155 (1997).

Hamill, O.P., Marty, A., Neher, E, Sakmann, B., and Sigworth, F.J. Improved patch clamp techniques for high resolution current recordings from cells and cell–free membrane patches. *Pflugers Arch.* 391:85–100 (1981).

Egan, M.E. et al. Defection regulation of outwardly rectifying chloride channel by protein kinase A corrected by insertion of CFTR. *Nature* 358:581–584 (1992).

(List continued on next page.)

*Primary Examiner*—Bennett Celsa
*Attorney, Agent, or Firm*—Deborah A. Dugan

[57] ABSTRACT

Methods and compositions for treating CF by mobilizing mutant forms of CFTR, which retain at least some functional activity, to the plasma membrane where they can mediate chloride ion transport are disclosed.

6 Claims, 14 Drawing Sheets

OTHER PUBLICATIONS

Anderson, M.P. et al. Demonstration that CFTR is a chloride channel by alteration of its anion selectivity. *Science* 253:202–205 (1991).

Nadler, S.G. et al. Elucidating the Mechanism of Action of the Immunosuppressant 15–Deoxyspergualin. *Therapeutic Drug Monitoring* 17:700–703 (1995).

Halloran, P.F. Molecular mechanisms of new immunosuppressants. *Clinical Transplantation* 10:118–123 (1996).

Edgington, S.M. Therapeutic Applications of Heat Shock Proteins. *Bio/Technology* 13:1442–1444 (1995).

Sheppard D.N. and Ostedgaard, L.S. Understanding how cystic fibrosis mutations cause a loss of Cl–channel function. *Mol. Med. Today* 2(7):290–297 (1996).

Yang et al., PNAS USA vol. 90 pp. 9480–9484 (Oct. 1993).

Brown et al., Cell Stress & Chaperones (1996) 1(2) 117–125.

5,985,824

METHODS AND COMPOSITIONS FOR TREATING CYSTIC FIBROSIS

This application of a CIP of Ser. No. 08/807,398 filed Feb. 27, 1997, now U.S. Pat. No. 5,834,421.

BACKGROUND OF THE INVENTION

Cystic Fibrosis (CF) is the most common fatal genetic disease in humans (Boat et al. (1989), Cystic Fibrosis, In: THE METABOLIC BASIS OF INHERITED DISEASE, Scriver, Beaudet, Sly and Valle, eds., McGraw Hill, New York, pp. 2649–2860). Based on both genetic and molecular analysis, a gene associated with CF was isolated as part of 21 individual cDNA clones and its protein product predicted (Kerem et al. (1989), Science 245: 1073–1080; Riordan et al. (1989), Science 245: 1066–1073; Rommens et al. (1989), Science 245: 1059–1065).

The product of the CF-associated gene, the cystic fibrosis transmembrane conductance regulator (CFTR), is a protein of approximately 1480 amino acids made up of two repeated elements, each having six transmembrane segments and a nucleotide binding domain. The two repeats are separated by a large, polar, so-called R-domain containing multiple potential phosphorylation sites. Based on its predicted domain structure, CFTR is a member or a class of related proteins which includes the multi-drug resistance (MDR) or P-glycoprotein, bovine adenyl cyclase, the yeast STE6 protein as well as several bacterial amino acid transport proteins (Riordan et al., supra; Hyde et al. (1990), Nature 346: 362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan et al., supra; Frizzell et al., supra.; Welsh and Liedtke (1986), Nature 322: 467; Li et al. (1988), Nature 331: 358–360; Hwang et al. (1989), Science 244: 1351–1353).

Sequence analysis of the CF associated gene has revealed a variety of mutations (Cutting et al. (1990a), Nature 346: 366–369; Cutting et al. (1990b), Am. J. Hum. Genet. 47: 213; Dean et al. (1990), Cell 61: 863–870; Kerem et al. (1989), Science 245: 1073–1080; and Kerem et al. (1990), Proc. Natl. Acad. Sci., USA 87: 8447–8451). Mutations in the gene encoding CFTR result in the synthesis of aberrant variants that are either unstable, mislocalized, or whose Cl$^-$ channel activity is dysfunctional as a consequence of defective regulation or conduction (Welsh and Smith (1993), Cell 73: 1251–1254). Over 200 different mutations have been described to date, but by far the most prevalent is a deletion of the three nucleotides that encode phenylalanine at position 508 (Phe$^{508}$) located within the first nucleotide binding domain of CFTR (Tsui, L. C. (1992), Hum. Mutat. 1: 197–203). The Phe$^{508}$ deletion (ΔF508) is associated with approximately 70% of the cases of cystic fibrosis.

Studies on the biosynthesis (Cheng et al. (1990), Cell 63: 827–834; Gregory et al. (1990), Nature 347: 382–386) and localization (Denning et al. (1992), J. Cell Biol. 118: 551–559) of ΔF508, as well as other CFTR mutants, indicate that many CFTR mutant proteins are not processed correctly and, as a result, are not delivered to the plasma membrane (Gregory et al., supra). These conclusions are consistent with earlier functional studies which failed to detect cAMP stimulated Cl$^-$ channels in cells expressing CFTR ΔF508 (Rich et al., supra; Anderson et al. (1991), Science 251: 679–682).

It is believed that the deletion of residue 508 in ΔF508-CFTR prevents the nascent protein from folding correctly, and consequently the variant is recognized by the quality control mechanism present within the endoplasmic reticulum (ER) to select out against misfolded or mutant proteins (Cheng et al. (1990), supra.; Gregory et al. supra.). The mutant ΔF508-CFTR bears carbohydrate structures characteristic of glycosylation at the ER and is eventually degraded. The inability of this mutant protein to exit the ER, to pass through the Golgi where it normally would be fully glycosylated, and traffic to the plasma membrane most likely accounts for the defective Cl$^-$ transport found in CF epithelia harboring this mutation (Quinton, P. M. (1990), FASEB J. 4: 2709–2727). Studies have shown, however, that ΔF508-CFTR, when presented at the plasma membrane is functional as a cAMP-responsive Cl$^-$ channel (Dalemans et al. (1991), Nature Lond. 354: 526–528; Denning et al., supra.; Pasyk and Foskett (1995), J. Cell. Biochem. 270: 12347–50).

Thus, there is a need in the art for methods and compositions which enable relocation of mislocalized CFTR mutants which retain at least some functional activity (i.e., ΔF508) to the plasma membrane of epithelial cells where they can effectively mediate chloride ion transport and restore sufficient membrane conductance. The present invention satisfies this need and provides related advantages as well.

SUMMARY OF THE INVENTION

The present invention pertains to methods for treating a subject having cystic fibrosis (CF). The methods involve the administration of an effective amount of an agent that facilitates the delivery of the mutant CFTR to the plasma membrane to the subject having CF. The agent interferes with and/or modulates the functioning of molecular chaperone proteins thereby allowing the mutant CFTR protein to escape from the ER, proceed to the plasma membrane and provide functional cAMP-responsive Cl$^-$ channels.

The present invention further pertains to a method for treating a subject's lung epithelia containing a mutant CFTR protein. The method involves contacting a subject's lung epithelia with an agent which interferes with and/or modulates the functioning of molecular chaperone proteins thereby allowing the mutant CFTR protein to escape from the ER, proceed to the plasma membrane and provide functional cAMP-responsive Cl$^-$ channels.

The present invention even further pertains to a method for treating a subject having CF by administering an effective amount of an agent that interferes with and/or modulates the functioning of molecular chaperone proteins thereby allowing the mutant CFTR protein to escape from the ER, proceed to the plasma membrane and provide functional cAMP-responsive Cl$^-$ channels.

Other aspects of the present invention include therapeutic compositions and packaged drugs for treating subjects having CF. The therapeutic compositions include a therapeutically effective amount of the aforementioned agents, and a pharmaceutically acceptable carrier. The packaged drug includes the aforementioned agents and instructions for administrating the agent for treating subjects having CF.

The present invention further provides methods and compositions for treating CF by mobilizing mutant forms of CFTR, which retain at least some functional activity, to the plasma membrane where they can mediate chloride ion transport are disclosed.

Accordingly, the invention described herein relates to methods and compositions useful for delivering mutant cystic fibrosis transmembrane regulator (CFTR) proteins, which retain at least some functional activity, to the plasma membrane of epithelial cells, where they can mediate chloride ion transport.

The above discussed and many other features and advantages of the present invention will become better understood by reference to the following detailed description when taken in conjunction with the accompanying drawings.

BRIEF DESCRIPTION OF THE DRAWINGS

FIG. 1A shows immunoprecipitation analysis of C127-ΔF508-low cells. FIG. 1B shows SPQ analysis using DSG concentrations 10–100 μg/ml. FIG. 1C shows SPQ analysis following treatment with 10 μg/ml DSG, sodium butyrate and growth at lowered temperature. FIG. 1D shows SPQ analysis following treatment with 10 μg/ml, 20 μg/ml and 50 μg/ml DSG. FIG. 1E summarizes the overall effects concentration of DSG on recombinant C127-ΔF508-CFTR cells at normal and reduced temperature.

FIG. 2A shows the shift in fluorescence in cells treated treated with DSG, growth at lowered temperature and control. FIG. 2B shows the percentage of responsive cells following treatment with different concentrations of DSG or growth at lowered temperature.

FIG. 9A shows the change in fluorescence in cells treated with DSG, growth at lowered temperature and control. FIG. 9B shows the percentage of responsive cells following treatment with different concentrations of DSG or growth at lowered temperature.

FIG. 10A shows representative whole cell currents under basal (unstimulated) conditions from IBE-1 cells. FIG. 10B shows a recording from the same IBE-1 cels. FIG. 10C shows whole cell currents from cells that had been treated with 10 μg/ml DSG for 48 h. FIG. 10D shows whole cell currents from cells treated with DSG following stimulation with 200 μM cpt-cAMP. FIG. 10E shows the current-voltage relationships obtained under basal conditions (squares) and after addition of 200 μM cpt-cAMP (circles) of 7 successfully patched cells from 7 different coverslips treated with DSG (10 μg/ml) for 48 to 72 h.

DETAILED DESCRIPTION OF THE INVENTION

Figure 1A:
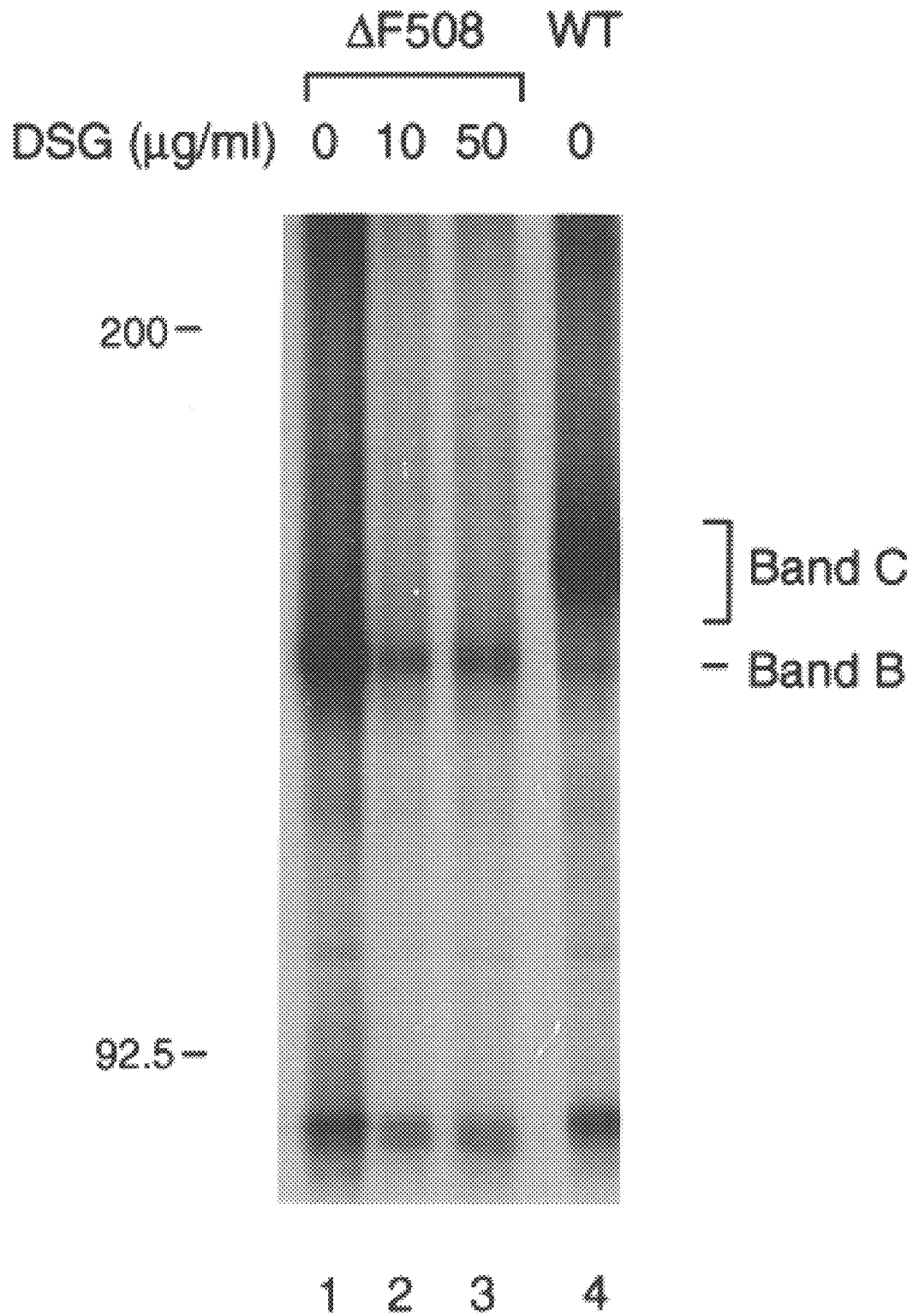
FIGS. 1A–1E show the effects of DSG on recombinant C127-ΔF508-CFTR cells.

All patent applications, patents, and literature references cited in this specification are hereby incorporated by reference in their entirety. In case of conflict or inconsistency, the present description, including definitions, will control.

The language "pharmaceutically acceptable salt" is art-recognized terminology. Typically these salts are capable of being hydrolyzed or solvated under physiological conditions. Examples of such salts include, sodium, potassium, and hemisulfate. The term further is intended to include lower hydrocarbon groups capable of being hydrolyzed or solvated under physiological conditions, i.e. groups which esterify the carboxyl group, e.g. methyl, ethyl, and propyl.

The chaperone modulating agents of the present invention can be purchased or alternatively can by synthesized using conventional techniques.

The language "effective amount" is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, and the selected route for administration of the agent. The determination of appropriate "effective amounts" is within the ordinary skill of the art.

The term administration is intended to include routes of administration which allow the agent (e.g., protein enhancing agent) to perform its intended function, e.g., increasing the level of at least one cellular protein. Examples of routes of administration which can be used include injection (subcutaneous, intravenous, parenterally, intraperitoneally, etc.), oral, inhalation, transdermal, and rectal. Depending on the route of administration, the agent can be coated with or in a material to protect it from the natural conditions which may detrimentally effect its ability to perform its intended function. The administration of the agent is done at dosages and for periods of time effective to significantly reduce or eliminate the symptoms associated with CF. Dosage regimes may be adjusted for purposes of improving the therapeutic response of the agent. For example, several divided doses may be administered daily or the dose may be proportionally reduced as indicated by the exigencies of the therapeutic situation.

The language "CF-associated cell" is intended to include a cell associated with CF which contains normal and/or mutant CFTR. Examples of such cells include airway epithelial cells such as nasal and lung epithelia.

The present invention further pertains to therapeutic compositions for treating a subject having CF. The composition contains a therapeutically affective amount of a chaperone modulating agent and a pharmaceutically acceptable carrier.

The language "therapeutically effective amount" is that amount sufficient or necessary to significantly reduce or eliminate a subject's symptoms associated with CF. The amount can vary depending on such factors as the severity of the symptoms being treated, the size of the subject, or the selected route for administration of the agent.

The language "pharmaceutically acceptable carrier" is intended to include substances capable of being co-administered with the agent and which allow the agent to perform its intended function, e.g. increasing the intracellular level of at least once cellular protein or inducing differentiation. Examples of such carriers include solvents, dispersion media, delay agents and the like. The use of such media and agents for pharmaceutically active substances is well known in the art. Any conventional media and agent compatible with the agent can be used with this invention. The agent of this invention can be administered alone or in a pharmaceutically accepted carrier. The agents further can be administrated as a mixture of agents which also can be in a pharmaceutically acceptable carrier. The agent further can be co-administered with other different art-recognized protein enhancing agents, differentiating agents, and/or adjuvants.

The present invention further pertains to a packaged drug for treating a subject having CF. The packaged drug includes a container holding an agent described above and instructions for administering the agent for treating a subject having CF. Examples of containers include vials, syringes, etc. The instructions would contain dosage information for administering the agent as described above.

One aspect of the instant invention provides that the molecular basis of most cystic fibrosis is the inability of the CFTR gene product to mature. That is to say, the failure of CFTR to move through the normal pathway of intracellular trafficking and modification means that the mature protein is absent from its final cellular destination in CF cells. In normal cells nascent CFTR interacts first with the endoplasmic reticulum and is then glycosylated at least one of Asn residues 894 and 900. The native molecule is then transported to the Golgi where carbohydrate processing to complex-type glycosylation occurs. Finally, at least some of the mature glycosylated molecule is thereafter transported to the plasma membrane.

It is now reasonably well established that the endoplasmic reticulum possesses a mechanism that prevents transport of mutant, misfolded or incorrectly complexed versions of proteins otherwise destined for further processing (Lodish, 1988; Rose and Doms, 1988; Pelham, 1989; Hurtley and Helenius, 1989; Klausner and Sitia, 1990). If this quality control mechanism operates on CFTR, it would prevent transport to the Golgi and consequently, further modification of several of the mutants reported here. As a result, the unmodified mutant versions of the protein either would not exit the endoplasmic reticulum and would subsequently be degraded therein, or alternatively, they would be transported to the lysosomes for degradation.

It is not clear how the quality control mechanism recognizes the difference between wild-type and those mutant versions of CFTR which were not further processed. One obvious mechanism would be that an alteration in structure of the molecule is detected. Indeed, gross changes in structure of the first nucleotide binding domain (and perhaps in consequence of the whole molecule) might be expected following deletion of phenylalanine 508. However, it is not clear how this change in structure would be detected by a mechanism located, for example, in the lumen of the endoplasmic reticulum, since the domain bearing the mutation, would lie on the cytosolic side of the membrane. Perhaps the structural change is transmitted across the membrane or perhaps the sensing mechanism does not recognize CFTR directly, but rather detects a protein with which it is complexed. In this case, all mutations within CFTR that prevent complex formation also prevent intracellular transport. Yet another mechanism would be that nascent CFTR has basal activity in the endoplasmic reticulum and that mutations that disrupt this activity are sensed by the quality control mechanism. Perhaps some activity of CFTR is necessary for its maturation and by this means, enzymatically inactive proteins are marked for degradation. Irrespective of the mechanism of discrimination, the time course of synthesis of both wild-type and mutant CFTR is notable in two respects. Firstly, the half life of band B is similar for both wild-type and mutant versions and secondly, most of the wild-type band B appears to be degraded. One interpretation of these results is that synthesis of CFTR involves two steps, retention in the endoplasmic reticulum during which time folding of the protein occurs followed by either export to the Golgi or degradation.

The most common cause of cystic fibrosis is deletion of the phenylalanine residue at position 508 ($\Delta$F508) of the cystic fibrosis transmembrane conductance regulator (CFTR). Studies have shown that this mutation results in the synthesis of a variant CFTR ($\Delta$F508-CFTR) that is defective in its ability to traffic normally to the apical membrane surface where it functions as a chloride (Cl$^-$) channel (Cheng et al. (1990), Cell 63: 827–834). Rather, most of the nascent $\Delta$F508-CFTR is retained in the endoplasmic reticulum (ER) where it is degraded by a process that involves ubiquitination (Jensen et al. (1995), Cell 83: 129–135; Ward et al. (1995), Cell 83: 121–127). However, functional cAMP-stimulated CFTR Cl$^-$ channel activity can be detected at the plasma membrane when, for example, $\Delta$F508-CFTR is synthesized at a reduced temperature (Denning et al. (1992), Nature 358: 761–764), or in the presence of chemical chaperones (Brown et al. (1996), Cell Stress & Chaperones 1: 117–125; Sato et al. (1996), J. Biol. Chem. 271: 635–638), and when overexpressed (Cheng et al. (1995), Am. J. Physiol. 268: L615–L624), indicating that the deletion of phenylalanine 508 does not completely abolish CFTR function. Therefore, strategies that facilitate the relocation or escape of mutant $\Delta$F508-CFTR from the ER to the plasma membrane may be therapeutically beneficial for the treatment of CF.

The mechanisms that result in the retention of the mutant CFTR in the ER have also been studied. The proper folding and assembly of many newly synthesized proteins in the ER is facilitated by molecular chaperones (Hartl, F. U. (1996), Nature 381: 571–580). These chaperones are thought to promote productive folding in part by preventing aggregation of folding intermediates. One explanation for the retention of CFTR mutations in the ER may be the presence of molecular chaperones in both the ER and the cytosol that prevent newly synthesized proteins from folding inappropriately during processing. Once a protein is correctly folded, it then moves to the Golgi. The immature or band B form of both wild-type CFTR and mutant $\Delta$F508-CFTR have been shown to interact with the ER-resident chaperone calnexin and the cytosolic chaperone hsp70 (Pind et al. (1994), J. Biol. Chem. 269: 12784–12788; Yang et al. (1993), Proc. Natl. Acad. Sci., USA 90: 9480–9484). However, only wild-type CFTR is able to dissociate from either calnexin and hsp70 and exit the ER. In contrast, mutant $\Delta$F508-CFTR is unable to dissociate from either calnexin or hsp70 and does not exit the ER to the Golgi. Both calnexin and hsp70 reportedly retain band B $\Delta$F508-CFTR in the ER and this, it is proposed, contributes to the mislocalization of the mutant CFTR. While interaction of most wild-type CFTR with hsp70 is transient, $\Delta$F508-CFTR forms a stable complex with hsp70 and is degraded in a pre-Golgi nonlysosomal compartment. In $\Delta$F508-CFTR producing cells, only the partially glycosylated band B form, and none of the fully glycosylated band C form of CFTR is generated (Cheng et al. (1990), Cell 63: 827–834). Presumably, the mutant $\Delta$F508-CFTR is recognized as abnormal, perhaps by the chaperones themselves, and is retained in the ER where it is subsequently degraded. The finding that hsp70 and calnexin may be responsible for the ER retention of $\Delta$F508-CFTR raises the possibility of therapeutic intervention in CF by agents capable of interfering with the normal functioning of these chaperones.

Given that $\Delta$F508-CFTR has been shown to be functionally competent when it is able to reach the plasma membrane, methods and compositions which promote trafficking of this mutant to the plasma membrane provide the basis of novel approaches to CF therapy. Accordingly, the present invention provides methods and compositions capable of disrupting the CFTR-molecular chaperone complex. For example, drugs active in altering the activity and distribution of hsp70 or calnexin proteins could advantageously be used to redistribute to the plasma membrane mutant CFTR which retains at least some functional activity. Similarly, agents effective in stimulating sufficient CFTR activity to result in export of otherwise mutant CFTR to the Golgi for additional glycosylation could result in improved CFTR function in homozygous CF individuals. Alternatively, therapeutic treatment via a suitable, therapeutically effective blocking agents could be used to deactivate chaperone proteins, for example, agents that are substrates and compete for binding to hsp70 or calnexin.

Examples of agents that bind to hsp70, include, but are not limited to deoxyspergualin (DSG), a spermidinyl, α-hydroxyglycyl, 7-guanidinoheptanoyl peptidomimetic, and analogs thereof, for example, methoxy- and glycylDSG have been shown to bind hsps with similar affinities (Nadler et al. (1992), *Science* 258: 484–486). Pure human hsp90 and hsp70 have equivalent affinities for DSG. Hsp90 is particularly abundant cytosolic protein and its concentration may approach 2–10 $\mu$M, while hsp70 can reach 5 $\mu$M. Given kds of 4–5 $\mu$M, the DSG-hsp complexes-would be highly populated and DSG could compete effectively for other protein and peptide binding to hsp70 and hsp90 and thereby affect protein trafficking (Nadeau et al. (1994), *Biochemistry* 33: 2561–2567).

DSG, a potent immunosuppressive agent, is a stable synthetic analogue of a natural product, spergualin, originally isolated from *Bacillus laterosporus* (Umezawa et al. (1981), *J. Antibiotics* 34: 1622–1624). DSG has demonstrated potent immunosuppressive activity in a number of T-cell dependent assays and models. It has been suggested that this immunosuppressive activity is mediated, at least in part, through its ability to interact with hsc70 and hsp90 (Nadler et al., supra; Nadeau et al., supra.). DSG has the unique ability to suppress both humoral and cell-mediated immune responses by down-regulating presentation of MHC class I or II antigen, modulating IL-1 production, and inhibiting IL-2 receptor expression. Perhaps most importantly it also has the effect of preventing monocytes from functioning as antigen-presenting cells.

It has been suggested that DSG works by blocking hsp70's ability to transport proteins, specifically NF-κβ into the nucleus (Tepper et al. (1995), *J. Immunol.* 155: 2427–2436). The working hypothesis is that DSG binds to hsc70, the constitutively expressed form of the hsp 70 family, that normally serves to fold and chaperone proteins across membranes. It appears that DSG is binding at a site normally occupied by the hsp helper protein dna J, interfering with ATPase activity in a still undetermined way (Nadler et al. (1995) *Therapeutic Drug Monitoring* 17: 700–703).

Accordingly, the present invention provides novel methods and compositions for treating cystic fibrosis-associated (CF-associated) cells with agents that interfere with and/or modulate the functioning of molecular chaperone proteins thereby allowing the mutant CFTR protein to escape from the ER, proceed to the plasma membrane and provide functional cAMP-responsive Cl⁻ channels.

In tests to ascertain whether binding of agents to the chaperones is sufficient to alter the trafficking and, hence, the subcellular location of ΔF508-CFTR, cells expressing the mutant protein were exposed to DSG. Results of experiments described herein show that addition of DSG to cells expressing recombinant ΔAF508-CFTR resulted in the appearance of functional cAMP-stimulated CFTR Cl⁻ channel activity at the cell surface. Moreover, DSG also restored cAMP-mediated CFTR Cl⁻ channel activity in human CF airway and biliary epithelial cells.

Discussion

Several therapeutic approaches are being developed concurrently for the treatment of CF. These include (i) agents that improve the anti-bacterial activity and viscosity of the mucus fluids lining the airways, (ii) agents that by-pass the CFTR Cl- channel defect, (iii) protein and gene augmentation therapy, and (iv) agents that reverse the mutant phenotype. Examples of the last group include aminoglycosides to suppress disease-associated stop mutations (Howard et al. (1996), *Nature Genetics* 2: 467–469) and phenylbutyrate (Cheng et al.(1995), supra; Rubenstein et al. (1996), *Pediat. Pulmonology* 13: 259) and chemical chaperones (Brown et al., supra.; Sato et al., supra.) to reverse trafficking mutants.

The trafficking, or Class II-type mutations as exemplified by ΔF508, are the most common among CF patients. The variant ΔF508-CFTR is recognized as abnormal and purportedly retained by the molecular chaperones hsp70 and calnexin in the ER where it is subsequently degraded (Yang et al. (1993), *Proc. Natl. Acad. Sci., USA* 90: 9480–9484; Pind et al. (1994), *J. Biol. Chem.* 269: 12784–12788). A premise of the present invention is, therefore, that agents capable of disrupting the interaction of ΔF508-CFTR with its molecular chaperones might facilitate escape of the variant protein from the quality control apparatus in the ER and, thereby, allow transit to the plasma membrane.

Deoxyspergualin, an immunosuppressant presently under clinical investigation, binds hsc70 and hsp90 with affinities that are predicted to complete effectively for the binding of these chaperones to nascent polypeptides (Nadeau et al., supra.). It is reported herein that DSG is indeed capable of partially reversing the trafficking defect associated with ΔF508-CFTR in recombinant and immortalized human CF epithelial cell lines.

ΔF508-CFTR cells exposed to DSG exhibited cAMP-stimulated Cl⁻ channel activity, a function that was otherwise lacking in these cells. These results are interpreted to mean that DSG was able to salvage a fraction of the mutant CFTR normally targeted for degradation by hsp70 and calnexin and, thereby, allowed for the translocation of at least some ΔF508-CFTR to the plasma membrane.

Although functional cAMP-stimulated Cl⁻ channels were detected in a proportion of the DSG-treated cells, the presence of any mature band C-form of CFTR could not be demonstrated by immunoprecipitation analysis. This result would argue that either a very small amount of ΔF508-CFTR that was below the level of detection using the biochemical assays escaped the ER to the Golgi and thence to the plasma membrane, or that the form that trafficked to the plasma membrane was indistinguishable from the core-glycosylated band B form. Although it is not unreasonable to speculate that DSG affected the trafficking and thereby the subcellular location of ΔF508-CFTR by altering its relationship with molecular chaperones, because of the inability to detect band C-CFTR, other mechanisms cannot be excluded.

The response observed with DSG was also compared with other interventions shown previously to result in the presence of ΔF508-CFTR at the plasma membrane. In both the CF airway and biliary epithelial cell lines, the response attained with DSG was comparable to that observed when these cells were cultured at a reduced temperature. In recombinant cells, the effect of incubation at low temperature has been shown to be as effective as treatment with the chemical chaperone glycerol in eliciting the presence of ΔF508-CFTR at the cell surface (Brown et al., supra.; Sato et al., supra.). In this regard, DSG would appear to be as effective as any other treatment shown previously to be capable of rescuing the ΔF508-CFTR trafficking defect.

If the mechanism by which DSG effected the presence of ΔF508-CFTR at the plasma membrane was indeed mediated through its interaction with the chaperones that normally associate with ΔF508-CFTR, then other interventions aimed at eliciting a similar release of the chaperones from the newly synthesized mutant CFTR might induce a portion of the protein to undergo maturation and transit to the cell surface. For example, heat shock treatment, which results in a rapid redistribution of hsp73 from the cytoplasm to the nucleus, might also result in the release of a small proportion of the mutant CFTR. Immunosuppressive Allotrap peptides derived from highly conserved regions of human MHC Class I molecules are capable of binding hsp70 and may also be similarly efficacious (Nossner et al. (1996), *J. Exp. Med.* 183: 339–348). However all of these interventions are non-specific, and as such are likely to result in a general disruption of the quality control apparatus that normally regulates proper folding and trafficking of proteins in the cell. It is unclear whether such a general disruption would adversely affect long term cell viability. Nevertheless, the results reported herein suggest that identification of agents like DSG that perhaps are more specific for ΔF508-CFTR or which act only transiently may be efficacious for the treatment of CF. Furthermore, because the mechanisms of action of sodium butyrate and the chemical chaperones are different from that of DSG, the use of a combination of these agents may be synergistic and result in even greater levels of ΔF508-CFTR at the plasma membrane. Finally, one may also consider inclusion of compounds like genistein and calyculin shown recently to enhance the activity of CFTR Cl channels at the cell surface (Yang et al. (1997), *Am. J. Physiol.* 272: C142–C155).

The following examples are intended to illustrate the invention without limiting the scope thereof.

Experimental Protocols

Assessment of CFTR functional activity using fluorescence digital imaging microscopy The cAMP-dependent CFTR Cl⁻ channel activity was assessed using the halide-sensitive fluorophore 6-methoxy-N-(3-sulfopropyl)-quinolinium (SPQ) essentially as described previously (Cheng et al., (1995), supra.; Marshall et al., supra.). Briefly, the cells were treated with different amounts of DSG for the times specified. At the end of the treatment period, the cells were loaded with SPQ by hypotonic shock for 4 min at room temperature. SPQ fluorescence initially was quenched by incubating the cells for up to 30 min in a NaI buffer (135 mM NaI, 2.4 mM $K_2HPO_4$, 0.6 mM $KH_2PO_4$, 1 mM $MgSO_4$, 1 mM $CaSO_4$, 10 mM dextrose, and 10 mM N-2 hydroxyethylpiperazine-N'2-ethanesulfonic acid, pH 7.4). After measuring the baseline fluorescence (Fo) for 2 min., the NaI solution was replaced with one containing 135 mM $NaNO_3$, and fluorescence was measured for another 16 min. Forskolin (20 μM) and 3-isobutyl-1-methyl-xanthine (IBMX) (100 μM) were added 5 min after the anion substitution to increase intracellular levels of cAMP.

An increase in halide permeability is reflected by a more rapid increase in SPQ fluorescence. It is the rate of change rather than the absolute change in signal that is the important variable in evaluating anion permeability. Differences in absolute levels reflect quantitative differences between groups in SPQ loading, size of cells, or number of cells studied. The data are presented as means± SE of fluorescence at time t (Ft) minus the baseline fluorescence (Fo, the average fluorescence measured in the presence of I⁻ for 2 min. before ion substitution) and are representative of results obtained under each condition.

For each experiment, between 50 to 100 cells were examined on a given day and studies under each condition were repeated on at least two days. For each experiment, the responses were compared with those obtained with control or untreated cells. Cells were scored as positive if they exhibited a rate of change in fluorescence that was greater than the signal observed with the control cells. Under the conditions specified above, control cells were unresponsive to added cAMP agonists. There was a broad spectrum in the rate of change in SPQ fluorescence observed with responsive cells. Normally, cells were scored as responsive if they generated a minimum of a 20° change in the rate of increase in SPQ fluorescence following stimulation with cAMP agonists. Because the response was heterogenous, the data shown are for the 10% of cells in each experiment showing the greatest response.

Whole cell patch-clamp recording

Whole cell patch-clamp recordings were performed essentially as described previously (Hamill et al., (1981), *Pflügers Arch.* 391: 85–100; Egan et al. (1992), *Nature* 358: 581–0584; Anderson et al. (1991), supra.; Sheppard et al., (1996). Briefly, cells on coverslips were placed in a chamber mounted on a Nikon Diaphot inverted microscope. Patch pipettes had resistances of 2–4 MΩ. Whole cell configuration was achieved with an additional pulse suction to rupture the gigaseal. The pipette (intracellular) solution contained: 130 mM CsCl, 20 mM TEA-Cl, 10 mM N-2-hydroxylethylpiperazine-N'-2-ethanesulfonic acid (HEPES), 10 mM ethylene glycol-bis-(β-aminoethylether) N, N, N', N'-tetraacetic acid (EGTA), 10 mM Mg-ATP, and 0.1 mM LIGTP, pH 7.4. The bath (extracellular) solution contained: 140 mM N-methyl-Dglucamine (NMDG), 2 mM $CaCl_2$, 1 mM $MgCl_2$, 0.1 mM $CdCl_2$, 10 mM HEPES, 4 mM CsCl, and 10 mM glucose, pH 7.4. These solutions were designed so as to study only currents flowing through Cl⁻ channels, since Cl⁻ was the only significant permeant ion in the solutions. Furthermore, $Ca^{2+}$-activated Cl⁻ currents were minimized by inclusion of 10 mM EGTA in the intracellular solution and 100 μM of $Cd^{2+}$ in the extracellular bath. $K^+$ currents were minimized by including 20 mM TEA in the intracellular solution. Aspartate was used as the replacement anion in experiments in which extracellular Cl⁻ concentration was changed. Forskolin (10 μM), IBMX (100 μM), 8-(4-chlorophenylthio)-cAMP (cpt-cAMP, 200 μM), diphenylamine carboxylic acid (DPC, 200 μM), UTP (100 μM), and ionomycin (1 μM) were added to the bath solutions as indicated. Current recordings were made from the same cells before, during, and after exposure to the solutions containing the different agonists or inhibitors. All experiments were performed at room temperature (22° C.). Currents were filtered at 2 kHz. Data acquisition and analysis were performed using the PCLAMP 5.5.1 software (Axon Instruments, Foster City, Calif.).

Biochemical Analysis of CFTR

Detailed procedures for preparing cell lysates, immunoprecipitation, phosphorylation of CFTR using protein kinase A and [γ³²P]ATP, and polyacrylamide gel electrophoresis have all been described previously (Cheng et al., (1995), supra.; Marshall et al., supra.).

Example 1

The Effect of DSG on Recombinant C127 Cells Expressing ΔF508 Cystic Fibrosis Transmembrane Regulator Protein Nadler et al. (1992), Science 258: 484–486 has reported that the immunosuppressant deoxyspergualin (DSG) interacts with hsc70, a member of the hsp70 family of heat shock proteins. The $K_d$ value for DSG binding to hsc70 is 4 μM, a concentration that is within the range of a pharmacologically active dose (Nadeau et al. (1994), Biochemistry 33: 2561–2567). Since the intracellular concentration of hsc70 is approximately 5μM, it is possible that DSG binding to hsp70 may compete effectively for peptide or protein binding to hsp 70.

Derivation of ΔF508–C127 Cells

A bovine-papilloma virus based eukaryotic expression vector (pBPV-CFTR-ΔF508) containing the gene for ΔF508 CFTR and neomycin resistance were transfected into C127 cells. The C127 cells are murine mammary cells which were obtained from ATCC (#CRL 1616). The expression of the mutant ΔF508 protein and neomycin was driven using a metallothionein promoter. Following transfection, clonal cells resistant to G418 were isolated and cells expressing the mutant ΔF508 protein were subsequently identified using antibodies specific for CFTR (mAb-13-1). The cells expressing the mutant ΔF508 CFTR protein were maintained in Dulbecco's modified eagle media (DMEM) supplemented with glutamine and fetal calf serum.

C127-ΔF508-low (mouse mammary tumor) is a recombinant cell line stably transfected with the cDNA encoding the mutant ΔF508-CFTR (Cheng et al. (1995), supra.; Marshall et al. (1994), J. Biol. Chem. 269: 2987–2995). These cells produce solely the immature, partially glycosylated band B form of CFTR (characteristic of processing only in the ER) and do not exhibit detectable CFTR Cl⁻ channel activity at the cell surface (Cheng et al. (1995), supra.). C127-mock is a cell line that has been stably transfected with the backbone of the expression vector used to generate C127-ΔF508-low (Cheng et al. (1995), supra.). LLCPK₁-ΔF508 (pig kidney epithelial) is a recombinant cell line stably expressing low levels of the mutant ΔF508-CFTR protein (Marshall et al., supra.). The details of the generation, characterization and routine propagation of these cell lines has been described (Cheng et al. (1995), supra.; Marshall et al., supra.).

Cells were treated with up to 100 μg/ml of DSG for up to 72 h. Concentrations of DSG >50 μg/ml were toxic to most of the cell types tested. Since DSG is modified by polyamine oxidase present in fetal bovine serum (Tepper et al., supra.), cells were routinely replenished with fresh medium containing DSG and aminoguanidine every 24 h. As a control in some experiments, C127 cells were also treated with 5 mM sodium butyrate for 24 h. to enhance expression of ΔF508-CFTR (Cheng et al. (1995), supra.). As another control, cells were cultured at 23° C. for 24 to 48 h. to facilitate folding of the mutant ΔF508-CFTR at the ER.

Treatment of the ΔF508–C127 Cells with DSG and Analysis of Cells for Chloride Channel Activity To test whether treatment with DSG may interfere with the ability of hsp70 to retain ΔF508-CFTR in the ER, recombinant C127 cells expressing ΔF508-CFTR were seeded onto glass coverslips and were exposed to DSG (10 to 100 μg/ml) (Bristol Myers Squibb, Seattle, Wa.) for 48 to 72 h. Analysis for evidence of mature band C-CFTR (Cheng et al. (1990), supra.) which would be indicative of processing of ΔF508-CFTR in the Golgi was performed. Biochemical analysis of the lysates from these cells showed no discernible evidence of the mature band C form of CFTR indicating that very little if any ΔF508-CFTR had exited the ER to the Golgi.

Immunoprecipitation analysis of C127-ΔF508-low cells

Lysates were prepared from C127 cells stably expressing ΔF508-CFTR (FIG. 1A, lanes 1–3) or wild-type CFTR (lane 4). Cells were treated with either 10 μg/ml DSG (lane 3) or left untreated (lanes 1 and 4) for 72 h before lysis. Immunoprecipitates obtained using the anti-CFTR monoclonal antibody mAB 24-1 (Marshall et al., supra.) were phosphorylated in vitro by the addition of the catalytic subunit of protein kinase A and [γ³²p]ATP. The positions of band B (core-glycosylated CFTR) and band C (mature form of CFTR) are indicated on the right.

Example 2

SPQ Analysis of C127-ΔF508-low Cells Following Treatment with DSG

To ascertain whether a small amount of ΔF508-CFTR, below the sensitivity of detection with the biochemical assay, may have traversed the Golgi to the plasma membrane the more sensitive single-cell membrane halide permeability assay using the Cl⁻ indicator SPQ (6 methoxy-N-(sulfopropyl)-quinolinium) (Cheng et al. (1995), supra.; Marshall et al., supra.; Cheng et al. (1991) Cell 66: 1027–1036). Accordingly, following treatment with DSG, the cells were assayed for the presence of functional CFTR chloride channel activity at the cell surface using the halide sensitive fluorophore SPQ assay. In this assay, a rapid change in SPQ fluorescence upon stimulation with cAMP agonists is indicative of the presence of active CFTR at the plasma membrane.

Cells were loaded with SPQ by either including 10 mM SPQ (Molecular Probes, Eugene, Oreg.) in the growth media for nine to twelve (or twelve to eighteen) hours or after hypotonic shock (with 50% vol/vol water) for 4 min at room temperature. SPQ fluorescence was initially quenched by incubating the cells for up to 30 min. in a sodium iodide buffer solution (135 mM NaI; 2.4 mM K₂HPO₄; 0.6 mM KH₂PO₄; 1.0 mM MgSO₄; 1.0 mM CaSO₄; 10 mM dextrose and 10.0 mM HEPES pH 7.4). After measuring the baseline fluorescence for two minutes using a Nikon inverted microscope, a Universal Imaging System and a Hamatsu camera, the sodium iodide buffer solution was replaced by a sodium nitrate buffer solution (same as the NaI solution except NaNO₃ was substituted for NaI) at time=0 min. and fluorescence was measured for an additional 16 minutes. SPQ fluorescence is quenched by iodide but not by nitrate. Intracellular cAMP levels were increased by adding forskolin (Calbiochem, San Diego, Calif.) and 3-isobutyl-1-methyl-xanthene (IBMX) (Sigma, St. Louis, Mo.) after the anion substitution at time=4 min. In this assay (hereinafter the SPQ assay) an increase in halide permeability results in SPQ fluorescence.

Figure 1B:
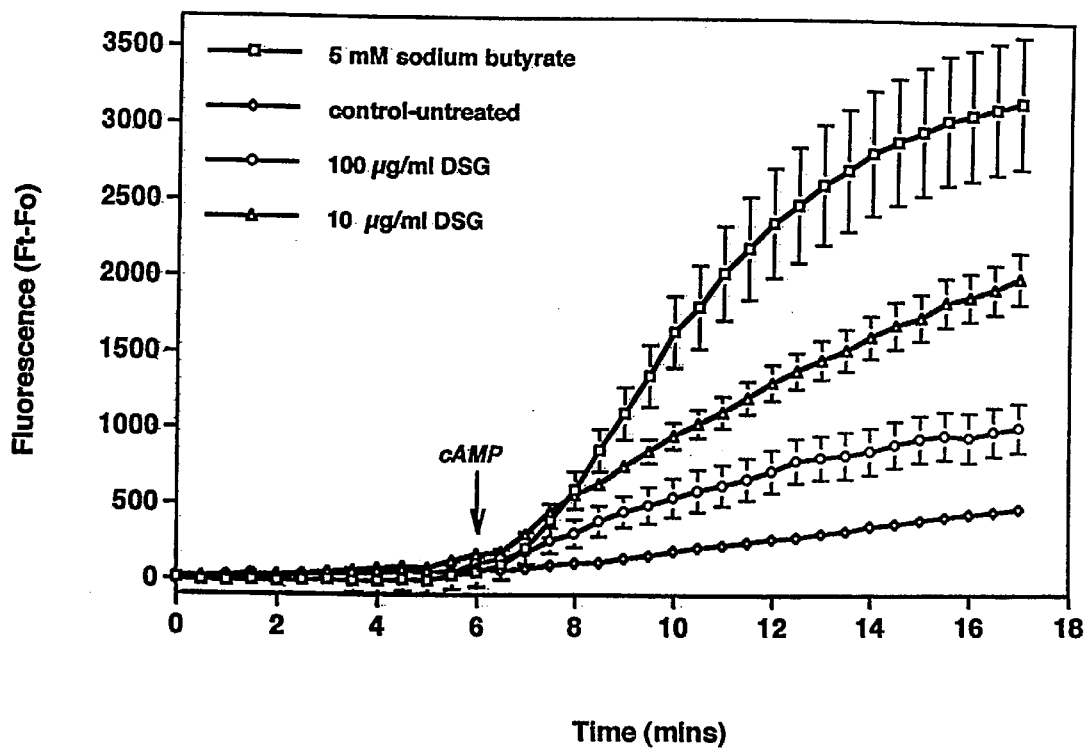

In this assay, a rapid change in fluorescence upon stimulation with cAMP agonists (i.e., forskolin) is indicative of the presence of active CFTR at the plasma membrane. FIG. 1B shows that DSG-treated C127-ΔF508-CFTR cells gave a rapid change in fluorescence following stimulation with forskolin indicating that incubation with DSG effected the presence of functional CFTR activity at the cell surface.

These cells, therefore, contained functional cAMP-dependent chloride channels. This activity was absent from ΔF508-C127 cells which had not been pretreated with DSG, but had been mock treated with phosphate buffered saline.

Example 3

The Effect of DSG Concentration on Recombinant C127 Cells Expressing ΔF508 Cystic Fibrosis Transmembrane Regulator Protein Results similar to those in Example 2 were obtained in another experiment (FIGS. 1C and 1D) using different concentrations of DSG (10 μg/ml; 20 μg/ml; 50 μg/ml). More optimal responses were observed in cells that were treated with lower concentrations of DSG compared to higher concentrations of DSG. However, this difference could be attributed to cytotoxicity associated with higher concentrations of DSG. The results of the study, which are presented in FIG. 1E, also indicate that percentage of mature CFTR produced from CFTR-ΔF508 in the presence of DSG increases upon exposure to reduced temperatures.

Figure 1C:
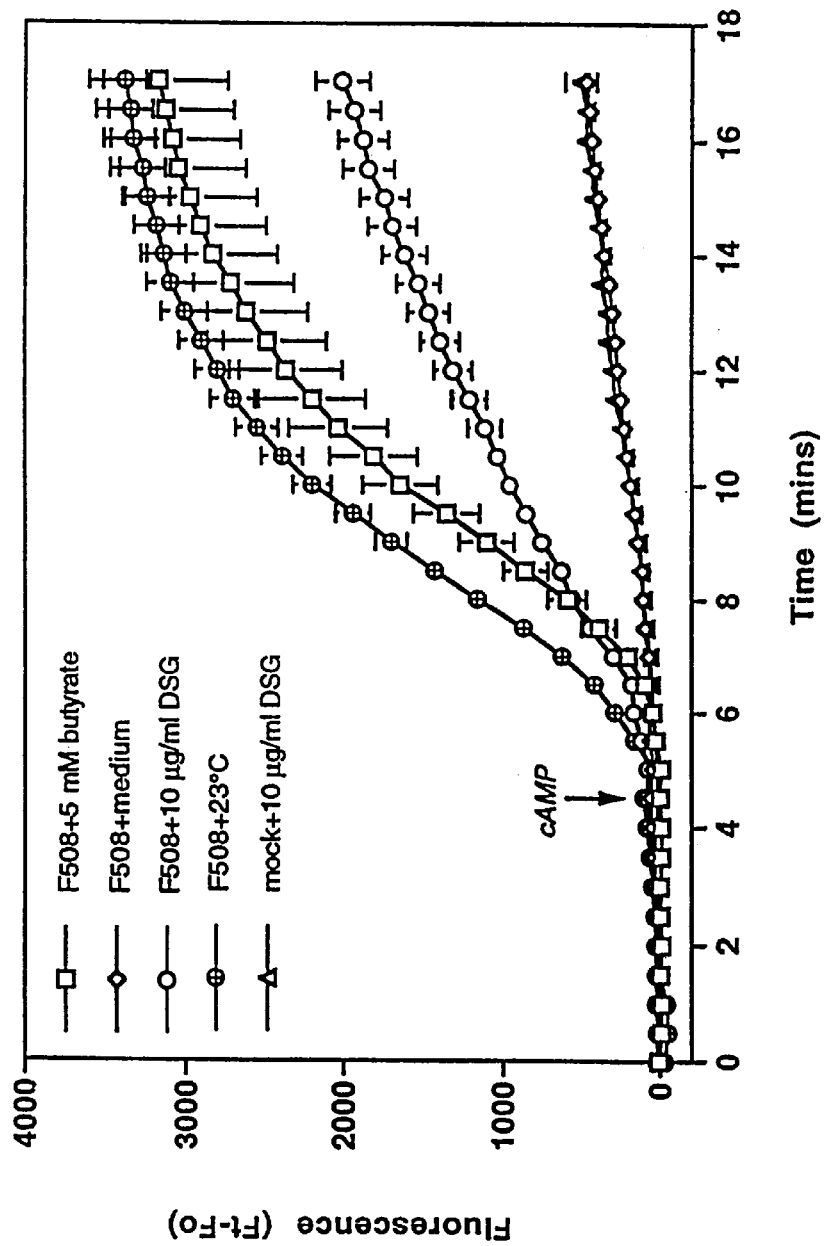
Figure 1D:
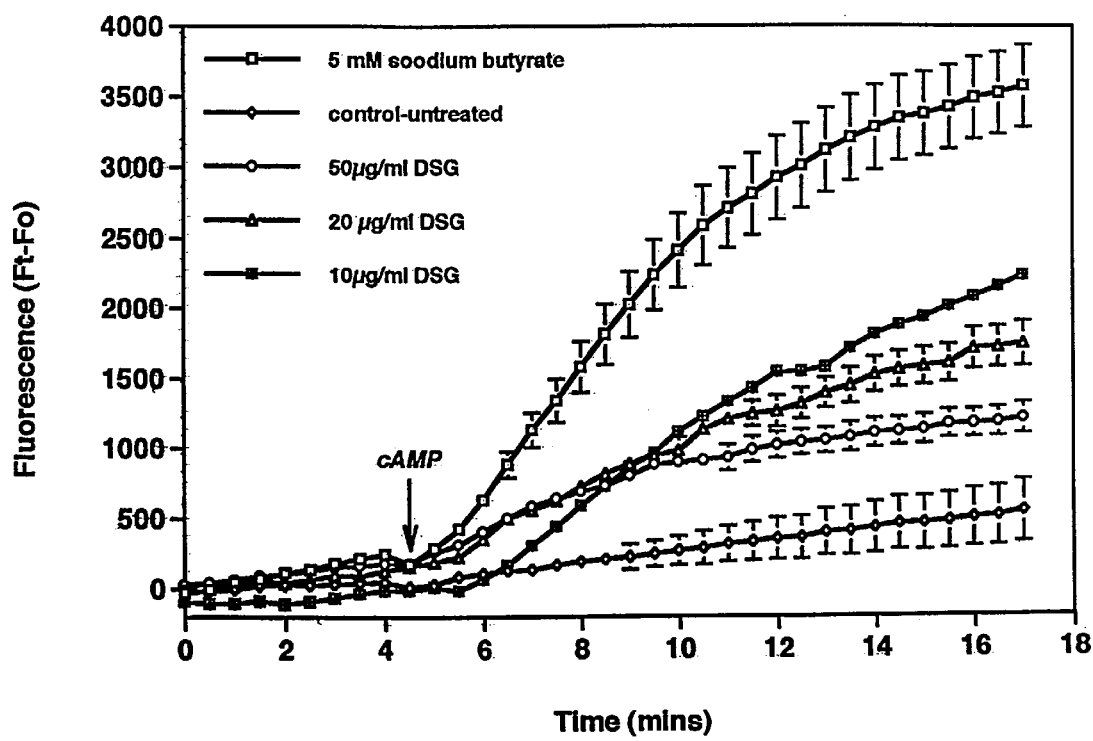
Figure 1E:
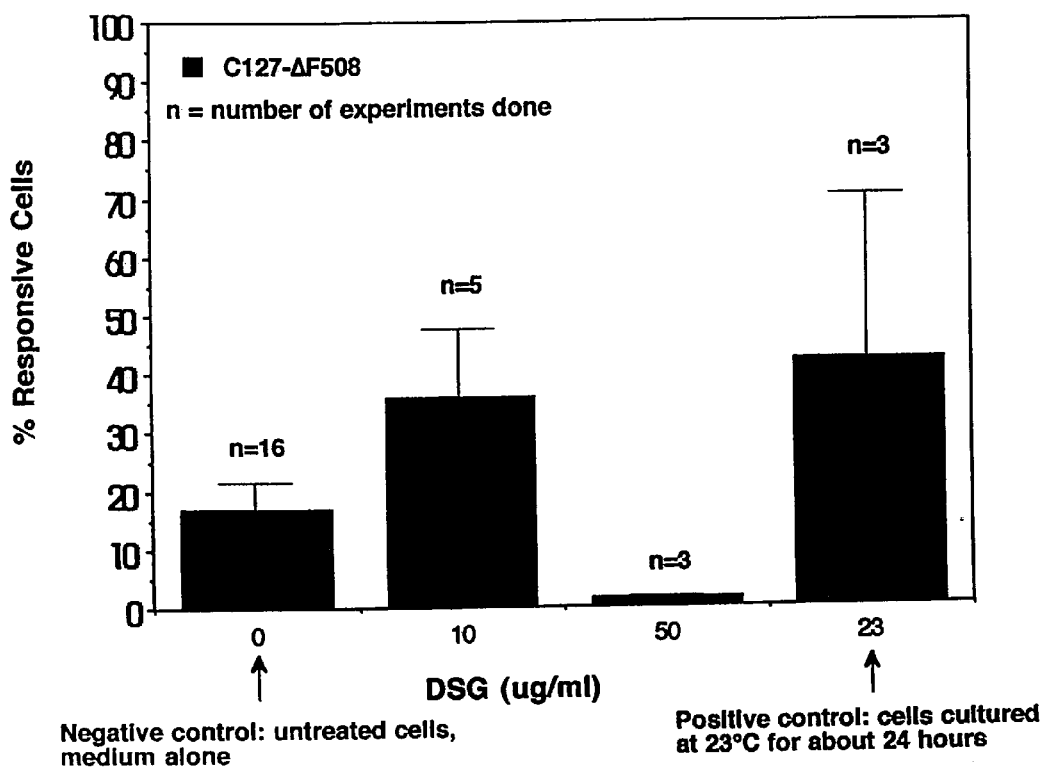

In FIG. 1C, change in fluorescence is shown for C127 cells expressing ΔF508-CFTR (n=9, where n=number of cells), cells expressing ΔF508-CFTR that had been treated with 5 mM sodium butyrate (Sigma) for 24 h. (n=11), or 10 μg/ml DSG (Bristol Myers Squibb) for 72 h (n=10), or incubated at 23° C. for 24 h. (n=12), and mock transfected C127 cells that had been similarly pre-treated with DSG (n=7). Data are presented as the fluorescence at time t (Ft) minus the baseline fluorescence (Fo, average fluorescence measured in the presence of I⁻ for 2 min. before ion substitution). Data are means±SEM and are representative of responses obtained from several experiments for each condition.

As previously reported (Cheng et al. (1995), supra.) either treating the ΔF508-CFTR-low cells with sodium butyrate to augment the expression of ΔF508-CFTR or culturing them at a reduced temperature (23° C.) to enhance folding (Denning et al., supra.) generated cAMP-stimulated halide efflux. Cells that were grown in the presence of DSG for 3 days also restored cAMP-stimulated anion efflux albeit to a lesser extent than was observed with sodium butyrate treatment or following a temperature shift. Approximately 17% of the DSG-treated C127AF508-CFTR-low cells generated a measurable response as compared to 90% with sodium butyrate treatment or following growth at low temperature (average of 5 experiments). This disparity in response was not unexpected since treatment of these cells with sodium butyrate or growth at reduced temperature, unlike treatment with DSG, results in synthesis of detectable amounts of band C-CFTR (Denning et al., supra.; Cheng et al. (1995); supra.). Exposure to higher concentrations of DSG (>50 μg/ml) was toxic to the cells and did not improve either the intensity or frequency of the signal. (FIGS. 1D and 1E) No response was observed in C127-ΔF508-low cells that were left untreated or in C127-mock cells (parental C127 cells mock transfected with expression vector alone) that had been treated with DSG (FIG. 1C). These results suggest that the Cl⁻ channels observed in the DSG-treated C127-ΔF508-low cells were most likely due to the presence of mutant ΔF508-CFTR at the cell surface.

Since the structure of DSG resembles that of the polyamine spermidine, C127-ΔF508-low cells were also treated with 5 μg/ml spermidine for 72 h. as a negative control. No measurable cAMP-stimulated Cl⁻ channel activity was detected following treatment with spermidine, arguing against a non-specific effect. Data similar to those described for C127-ΔF508-low cells were also observed with LLCPK₁-ΔF508 cells, a recombinant pig kidney epithelial cell line stably expressing the variant CFTR.

Under the conditions tested, the change in SPQ fluorescence observed in DSG-treated cells was less than that obtained with sodium butyrate, an agent described previously as capable of effecting the presence of ΔF508-CFTR at the plasma membrane of these cells (Cheng et al. (1995), *Am. J. Physiol.* 268: L615–L624). It is possible that with optimization of the dose of DSG, and addition of the polyamine oxidase inhibitor aminoguanidine hemisulfate to prevent the breakdown of DSG (Tepper et al. (1995), *J. Immunol.* 155: 2427–2436), greater responses may be realized. Furthermore, because the mechanism of action of butyrate and DSG are likely to be different, use of both agents together may be synergistic and result in even greater levels of ΔF508-CFTR at the plasma membrane.

Example 4

The Effect of DSG on Immortalized Human Airway Epithelial Cells Expressing ΔF508 Cystic Fibrosis Transmembrane Regulator Protein Cell Culture CFT1 and JME/CF15 are two immortalized human CF airway epitheliavarill lines which contain the ΔF508 variant (Jefferson et al. (1990), *Am. J. Physiol.* 259: L496–L505; Yankaskas et al., (1993), *Am. J. Physiol.* 264: C1219–C1230). Cells were treated with up to 100 μg/ml of DSG for up to 72 h. Concentrations of DSG >50 μg/ml were toxic to most of the cell types tested. Since DSG is modified by polyamine oxidase present in fetal bovine serum (Tepper et al., supra.), cells were routinely replenished with fresh medium containing DSG and aminoguanidine every 24 h. As a control in some experiments, cells were cultured at 23° C. for 24 to 48 h. to facilitate folding of the mutant ΔF508-CFTR at the ER.

Immortalized CF nasal airway epithelial cells (JME/CF15) generated from a ΔF508 (−/−) patient, were maintained by coculturing with lethally irradiated NIH-3T3 cells in Dulbecco's modified eagles medium/F-12 (3:1) supplemented with adenine, insulin, transferrin, triiodothyronine, hydrocortisone, cholera toxin, epidermal growth factor and 5% fetal bovine serum. Before use cells were grown to confluence to eliminate all cocultured NIH-3T3 cells.

Figure 2A:
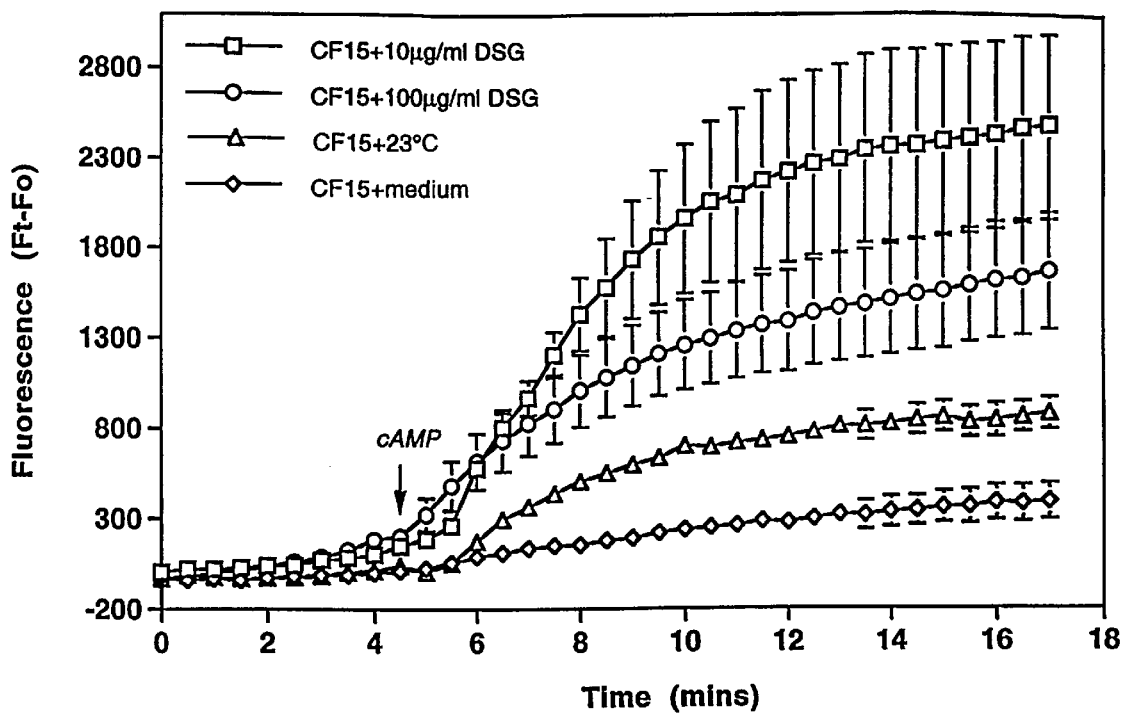
FIGS. 2A and 2B show the results of SPQ analysis of human CF airway epithelial cells following treatment with DSG.

Treatment of the JME/CF15 (or CFT1) Cells with DSG and Analysis of Cells for Chloride Channel Activity To test whether treatment with DSG had a similar effect on human CF cells, an immortalized airway epithelial cell line (JME/CF15) obtained from a CF patient homozygous for the ΔF508 mutation was treated with DSG. Attempts to detect changes in the glycosylation state of CFTR following treatment with DSG or sodium butyrate or growth at reduced temperature by immunoprecipitation assays were unsuccessful due to the low amounts of CFTR in these cells. This was not surprising since many similar labeling experiments in the past using primary normal human airway epithelial cells also failed to detect CFTR due to its low abundance. Examination of the untreated JME/CF15 cells using the SPQ assay showed, as expected, a lack of detectable cAMP-stimulated Cl⁻ channel activity (FIG. 2A).

Additionally, consistent with expectations, when these cells were grown at 23° C. for 24 h., measurable cAMP-regulated Cl⁻ channel activity could be detected in a proportion of the cells. Cells pre-treated with between 10 and 100 μg/ml DSG for 72 h. also displayed cAMP-responsive Cl⁻ channel activity. The effect was specific for DSG and was not replicated with the structurally related analogue spermidine.

Figure 2B:
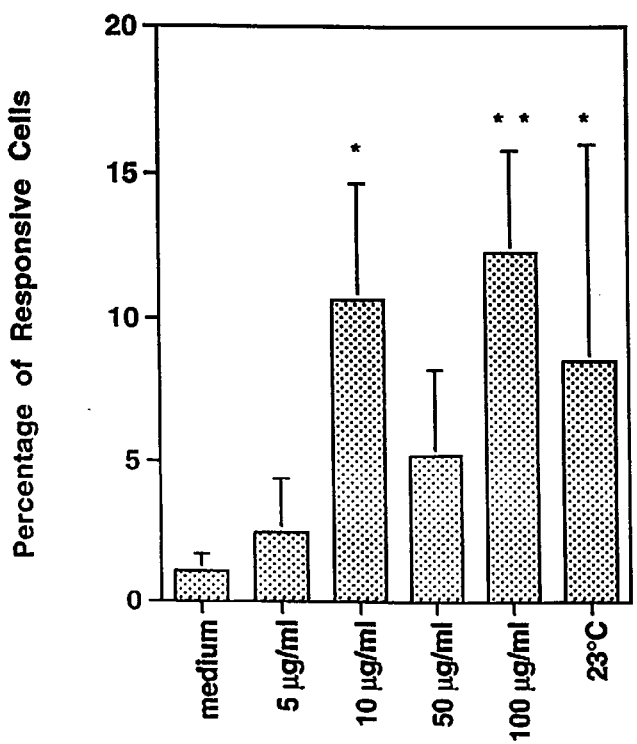

The response observed with DSG appeared more robust than that attained when cells were cultured at low temperature. For example, the cAMP-stimulated rate of change in SPQ fluorescence observed with DSG was consistently greater (FIG. 2A) and the total number of responsive cells (approximately 10–15%) was slightly higher (FIG. 2B) than that observed when the cells were cultured at low temperature. This is contrary to what was observed with the recombinant C127-ΔF508-low cells. However, it should be noted that DSG also has an ascribed role in blocking the nuclear translocation of the transcriptional factor NF-κB (Tepper et al., supra.). This block may have reduced the transcriptional activity of the CMV promoter (which contains several consensus NF-κB binding sites) used to express ΔF508-CFTR in the C127 cells and, therefore, reduced the levels of mutant protein produced in these cells. Although the percentage of responsive cells observed with DSG was only approximately 12% (FIG. 2B), it should be noted that this determination was limited by the sensitivity of the SPQ assay and that the number of cells affected may be greater.

Although a greater number of responsive cells was observed when 10 μg/ml of DSG was used instead of 5 μg/ml, no further significant increment in response was noted at concentrations higher than 10 μg/ml. It appears, therefore, that DSG would be capable of generating functional cAMP-stimulated Cl⁻ channel activity in at least a proportion of the immortalized ΔF508 human airway epithelial cells. Because many studies have indicated that these cells lack cAMP-dependent Cl⁻ channel activity other than CFTR (Jefferson et al., supra.), the observed response after DSG treatment was most likely due to ΔF508-CFTR at the cell surface. The above experiments have been repeated using another immortalized human CF airway epithelial cell line, CFT1, with very similar results.

To test whether treatment with DSG may interfere with the ability of hsp70 to retain ΔF508-CFTR in the ER, JME/CF15 (or CFT1) cells expressing ΔF508 CFTR were seeded onto glass coverslips and were exposed to DSG (10 μg/ml; 50 μg/ml; 100 μg/ml) (Bristol Myers Squibb, Seattle, Wash.) for 48 to 72 h.

Following treatment with DSG, the cells were assayed for the presence of functional CFTR chloride channel activity at the cell surface using the halide sensitive fluorophore 6-methoxy-N-[3-sulfopropyl]-quinolinium (SPQ) assay (Cheng et al. (1991) *Cell* 66: 1027–1036). See, also Example 2 above.

Figure 3:
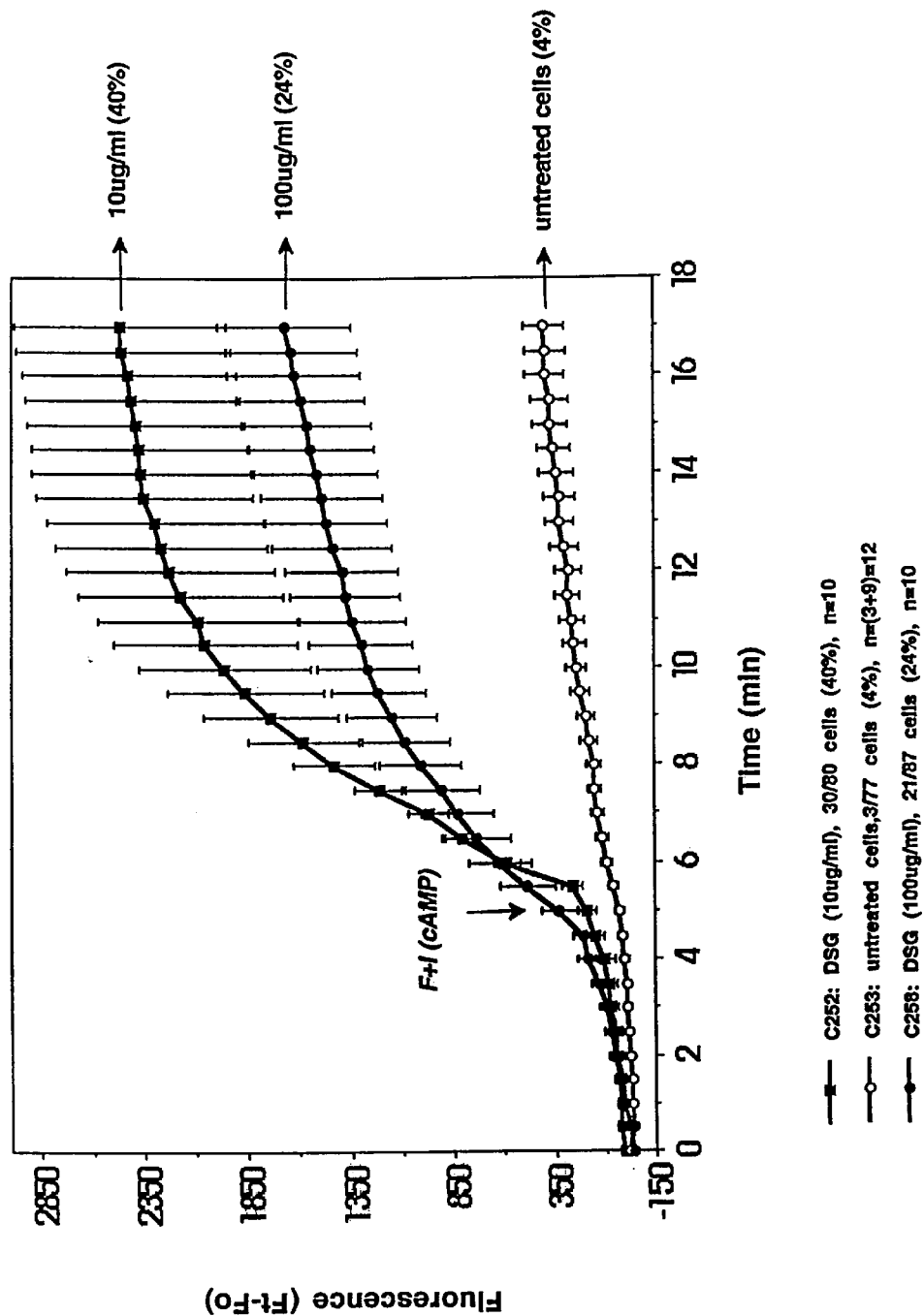
FIG. 3 shows the results of SPQ analysis of DSG treated JME15 cells.
Figure 4:
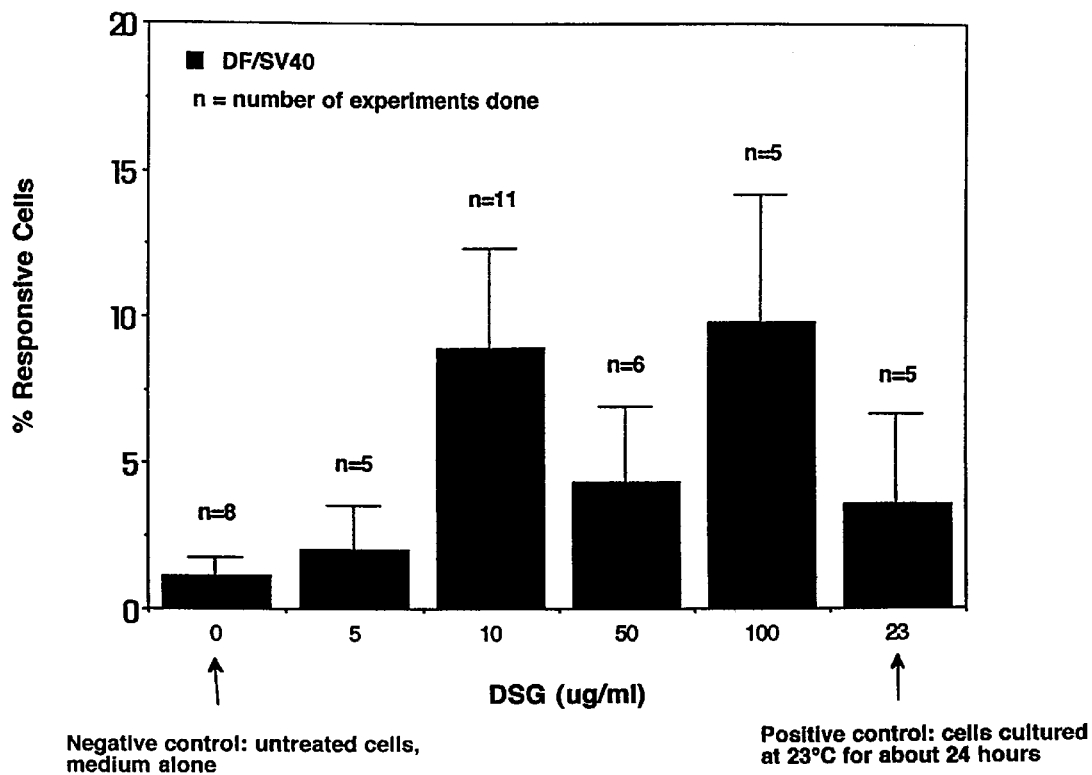
FIG. 4 shows the overall effects of varying concentrations of DSG on human JME/CF15 cells at normal and reduced temperature.

FIG. 3 shows that DSG at doses of 10, 50, and 100 μg/ml increased cAMP-mediated chloride channel activity in immortalized airway epithelial (JME/CF15) cells generated from a ΔF508 (−/−) patient measured by SPQ. The results of the study, which are presented in FIG. 4, indicate that percentage of mature CFTR produced from CFTRΔF508 in the presence of DSG increases upon exposure to reduced temperatures.

Figure 5:
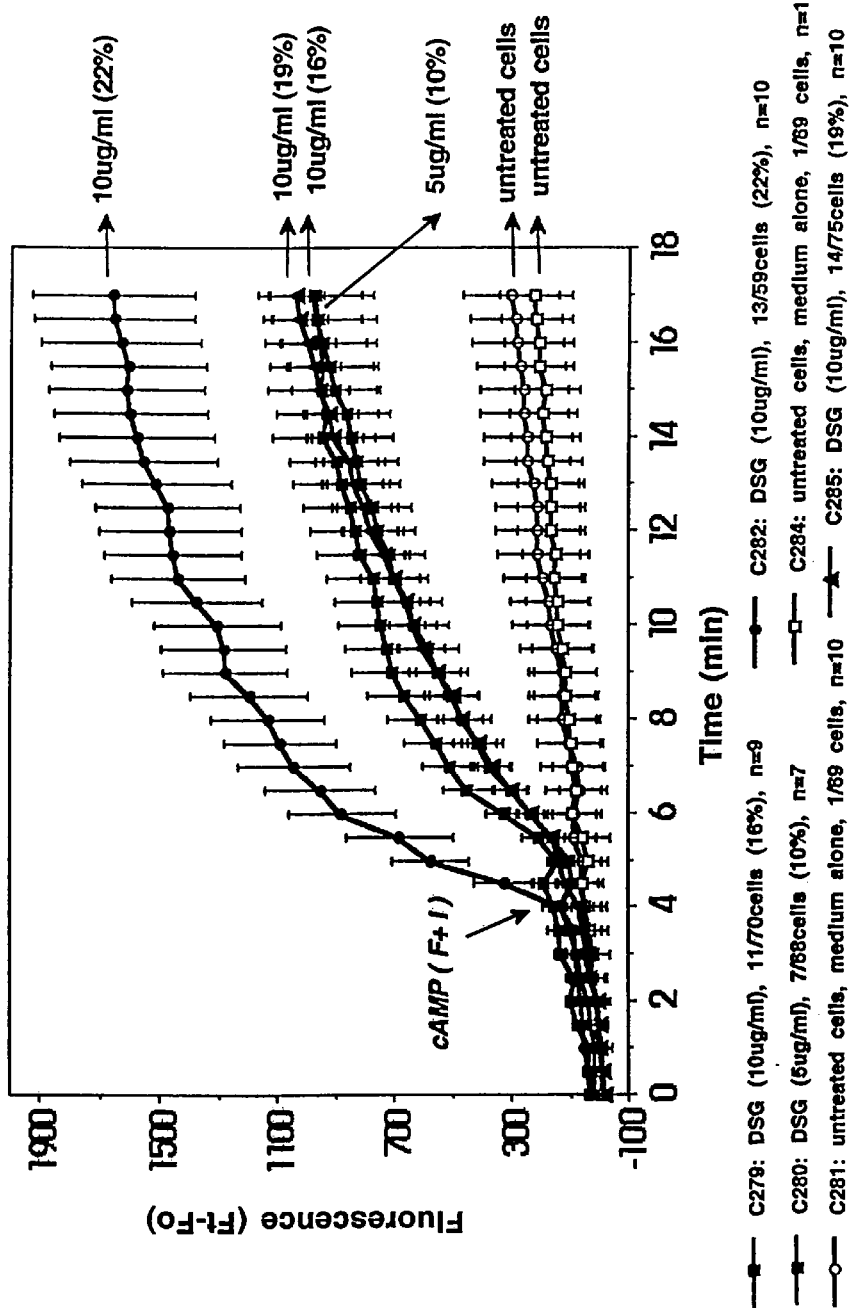
FIG. 5 shows the results of SPQ analysis of DSG treated SJBE cells.
Figure 6:
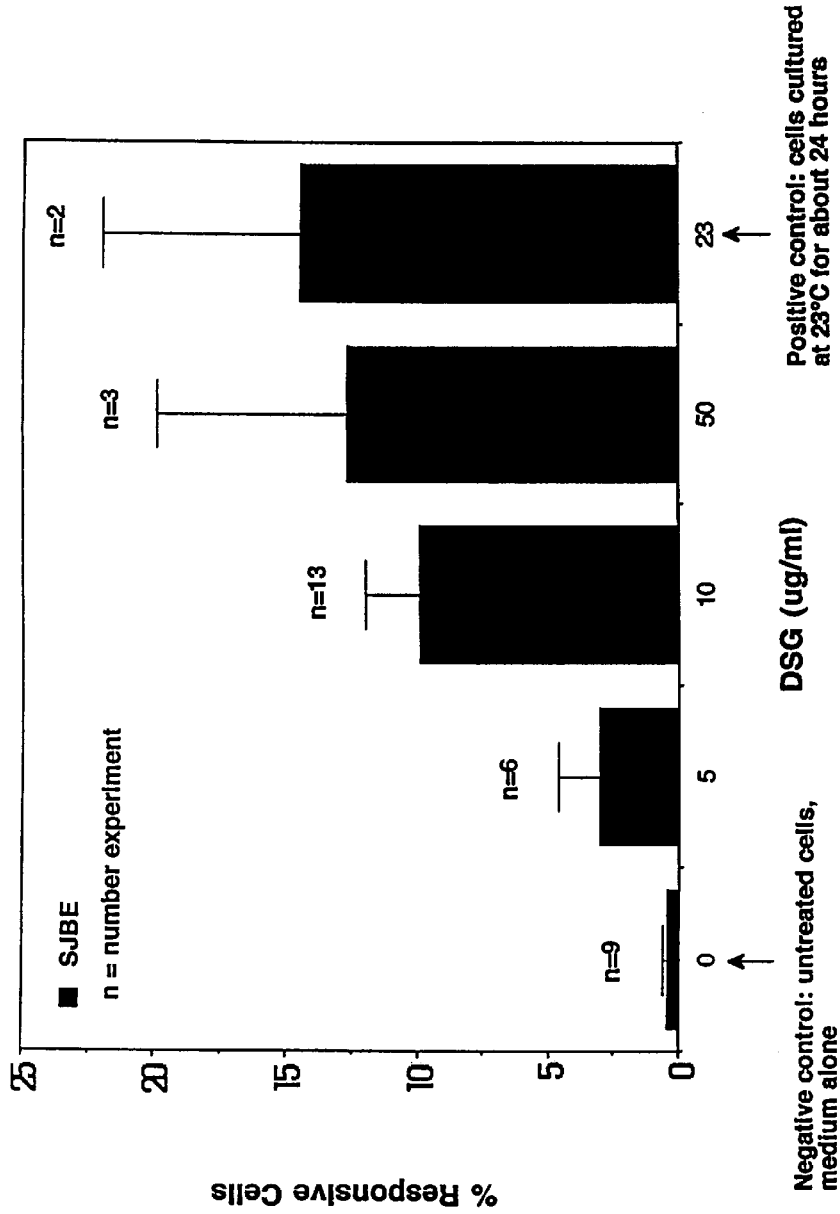
FIG. 6 shows the overall effects of varying concentrations of DSG on human SJBE cells at normal and reduced temperature.
Figure 7:
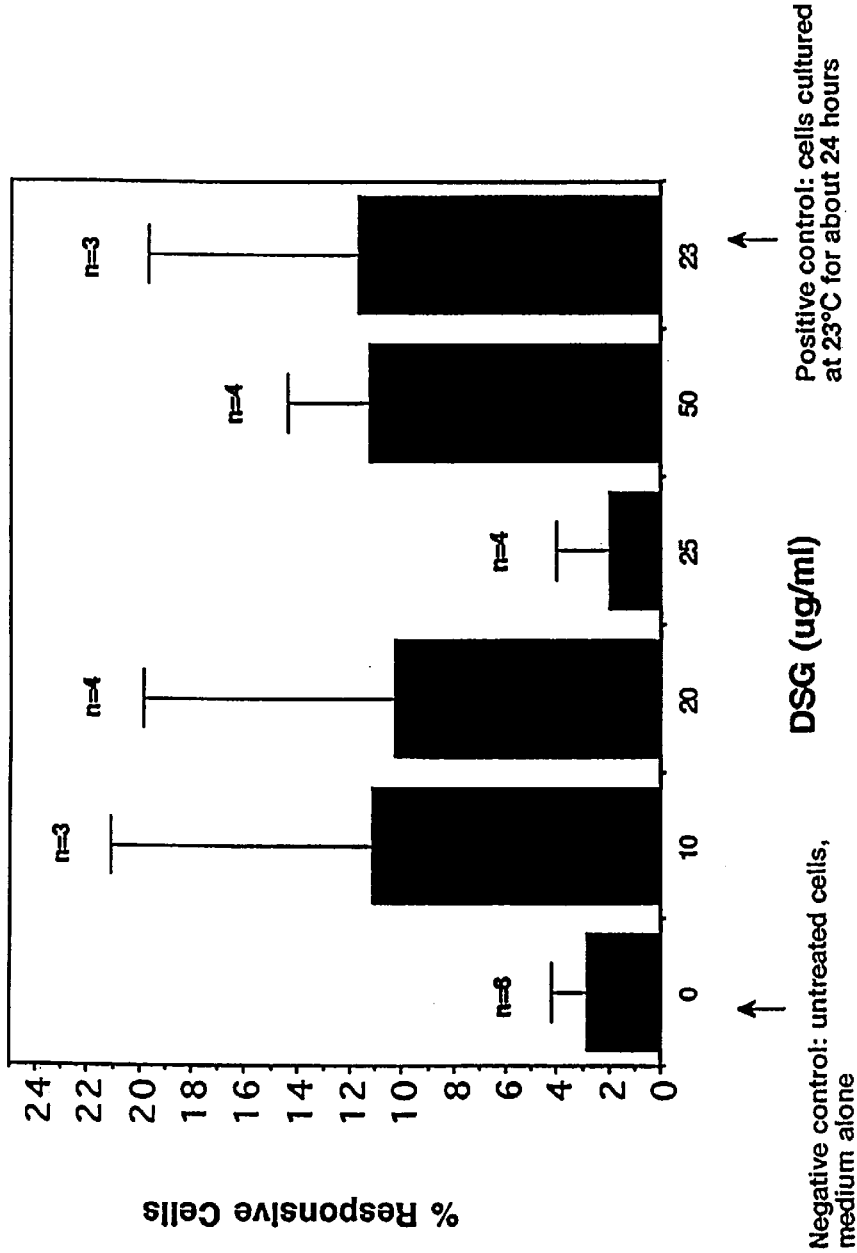
FIG. 7 shows the overall effects of varying concentrations of DSG on a bovine papilloma virus immortalized human airway epithelial cell line containing the ΔF508 variant.
Figure 8:
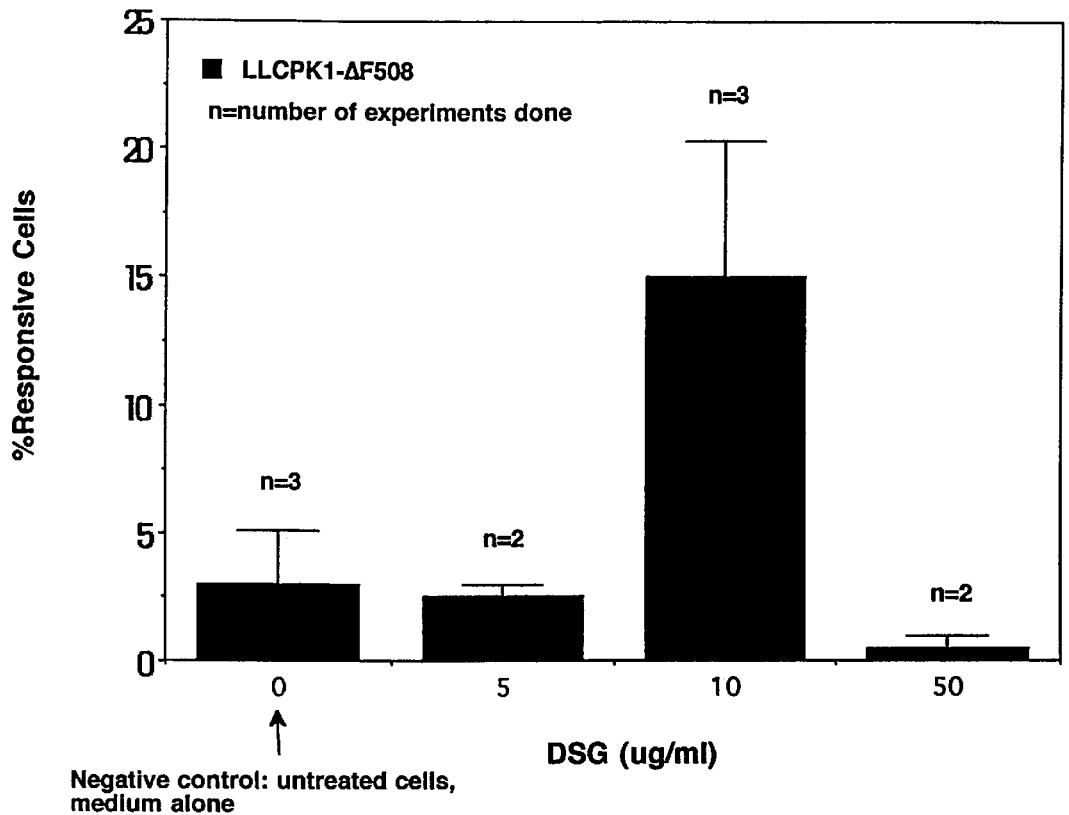
FIG. 8 shows the overall effects of varying concentrations of DSG on a pig kidney epithelial cell line containing the ΔF508 variant.

Similar results were obtained in an SV40 immortalized human intrahepatic biliary duct epithelial (SJBE) cell line containing the ΔF508 variant (FIGS. 5 and 6). However, in cell lines expressing recombinant ΔF508 under the control of a CMV promoter, namely C127 cells and LLCPK₁ cells, the effects of DSG on cAMP-mediated chloride channel activity measured by SPQ was marginal (FIGS. 7 and 8).

These results suggest that DSG may rescue ΔF508 CFTR by affecting its trafficking in immortalized human CF epithelial cells. The mechanism, possibly through an interaction with hsp 70, is different from that of sodium butyrate which has been shown to cause overexpression of ΔF508 in recombinant cells.

Example 5

The Effect of DSG on Primary Airway Epithelial Cells Expressing ΔF508 Cystic Fibrosis Transmembrane Regulator Protein To test whether treatment with DSG may interfere with the ability of hsp70 to retain ΔF508-CFTR in the ER, primary tracheobronchial epithelial cells from transgenic ΔF508 (−/−) mice are seeded onto glass coverslips and exposed to varying concentrations of DSG (10 μg/ml to 100 μg/ml) (Bristol Myers Squibb, Seattle, Wash.) for a period of 3–5 days.

Following treatment with DSG, the cells are assayed for the presence of functional CFTR chloride channel activity at the cell surface using the halide sensitive fluorophore 6-methoxy-N-[3-sulfopropyl]-quinolinium (SPQ) assay (Cheng et al. (1991) *Cell* 66: 1027–1036). See, also Example 2 above.

Example 6

The Effect of DSG on Immortalized CF Biliary Epithelial Cells

Cell Culture

Figure 9A:
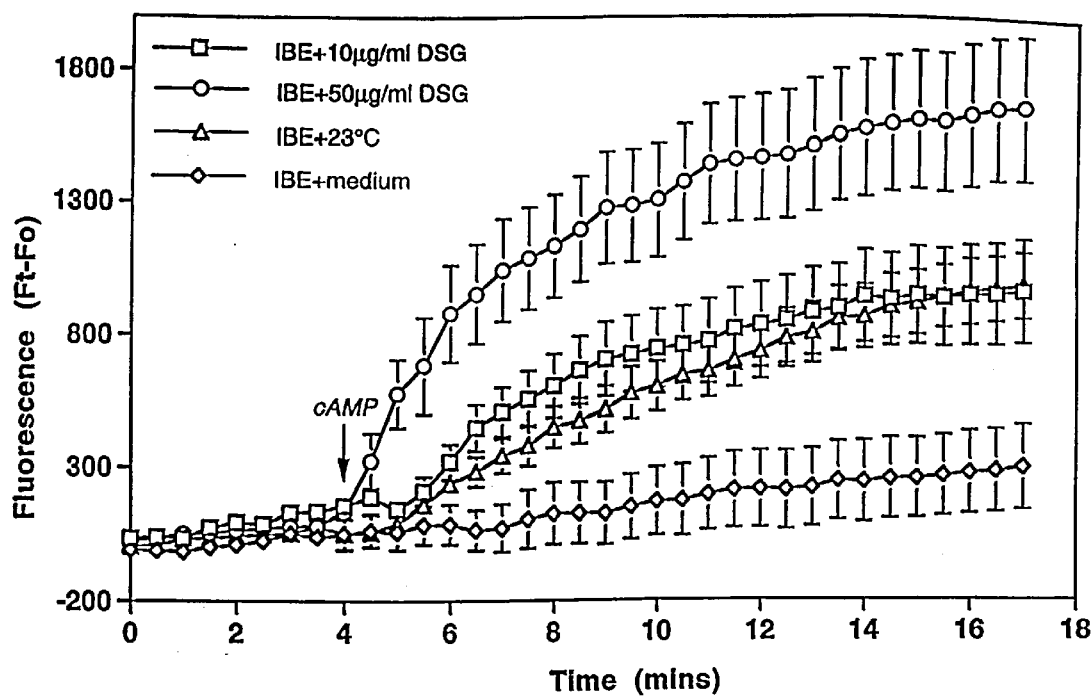
FIGS. 9A and 9B show the results of SPQ halide efflux assay of IBE-1 cells following treatment with DSG.
Figure 9B:
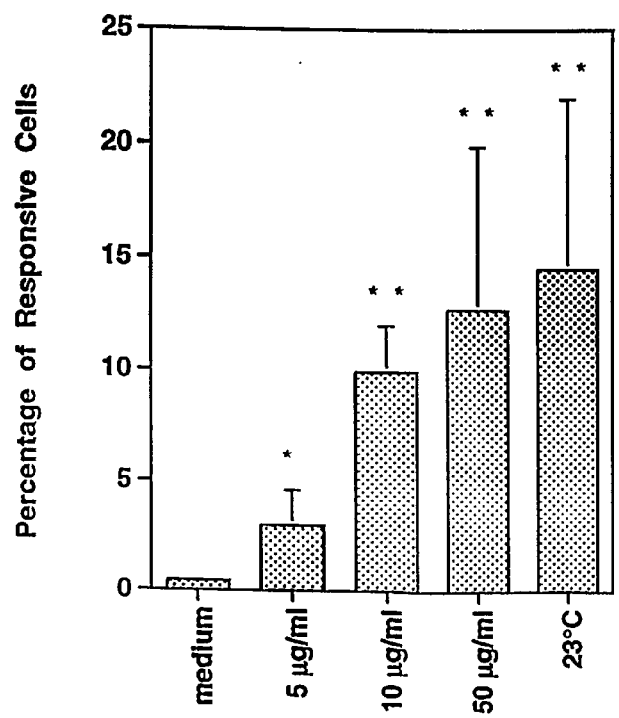
Figure 10:
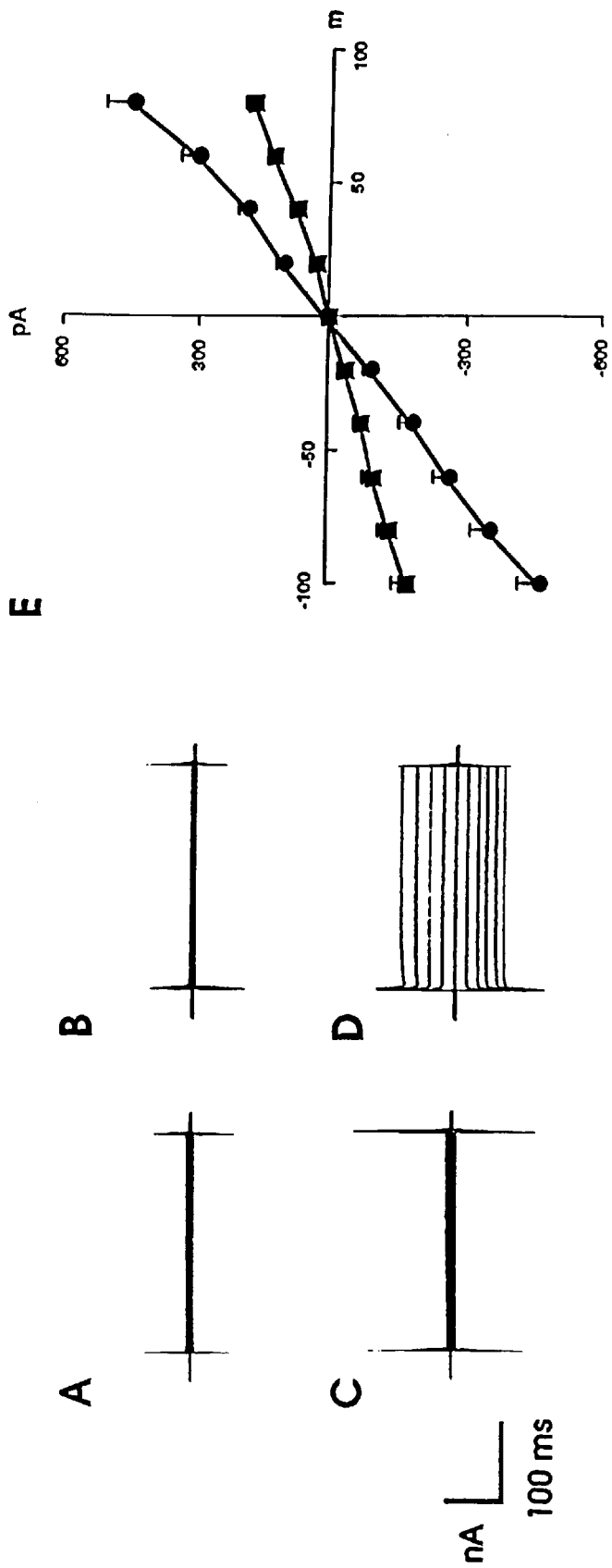
FIGS. 10A–10E show the results of whole cell patch-clamp analysis of IBE-1 cells.

IBE-1 is an immortalized human CF intrahepatic biliary epithelial cell line which contain the ΔF508 variant and G542X mutation (premature stop mutation at residue 542) (Grubman et al. (1995), *Gastroenterology* 108: 584–592). Cells were treated with up to 100 μ/ml of DSG for up to 72 h. Concentrations of DSG >50 μg/ml were toxic to most of the cell types tested. Since DSG is modified by polyamine oxidase present in fetal bovine serum (Tepper et al., supra.), cells were routinely replenished with fresh medium containing DSG and aminoguanidine every 24 h. As a control in some experiments, cells were cultured at 23° C. for 24 to 48 h. to facilitate folding of the mutant ΔF508-CFTR at the ER.
Treatment of the IBE-1 Cells with DSG and Analysis of Cells for Chloride Channel Activity The ability of DSG to influence the presence of endogenous mutant ΔF508-CFTR at the plasma membrane cAMP-stimulated Cl⁻ channel activity also assessed in IBE-1 cells. Consistent with previous reports (Grubman et al., supra.), IBE-1 cells did not exhibit any measurable cAMP-stimulated Cl⁻ channel activity (FIG. 9A). However, upon exposure to between 5 and 50 μg/ml DSG for 72 h., up to 20% of the cells exhibited measurable cAMP-stimulated Cl⁻ channel activity (FIG. 9B). The effect of DSG on IBE-1 cells was concentration-dependent, with higher concentrations of DSG giving rise to greater transport rates and higher numbers of positively-responding cells. Moreover, the response observed at the higher concentrations was similar to that attained when these cells were cultured at reduced temperature.
Whole Cell Patch-Clams Analysis of IBE-1 Cells Treated with DSG Whole cell patch experiments were performed to further demonstrate the presence of functional CFTR across the cytoplasm in cells treated with DSG. In all of the successfully patched CF IBE-1 cells from 6 separate coverslips no activation of whole cell currents in response to forskolin (10 μM) plus IBMX (100 μM) or cpt-cAMP (200 μM) was detected (FIG. 10A and 10B), indicating no endogenous CFTR channel activity in these cells. In contrast, in 7 out of 19 successful patched cells from 19 separate coverslips treated with DSG (10 μM) for 48 to 72 hrs. a significant activation of whole cell currents was observed. One of the representative experiments is shown in FIG. 10C and 10D. As all the other cells, the holding potential was 0 m, which inactivated the voltage-gated Na$^+$ and Ca$^{++}$ channels. After addition of 200 μM cpt-cAMP to the bath solution, voltage steps from the holding potential to between −100 mV and 80 mV in 20 mV increments activated whole cell currents. In these experiments, the intracellular and extracellular solutions were designed to study only current flowing through Cl$^-$ channels, since Cl$^-$ is the only significant permeant ion in solution. Ca$^{++}$ and K$^+$ currents were minimized by 100 μM of extracellular Cd$^{++}$ and 20 mM of intracellular TEA respectively. Furthermore, the currents were ascertained to be Cl$^-$ currents from change in the reversal potential which was shifted from 1.1±1.5 to 47.3±6.1 mV by reducing extracellular Cl$^-$ from 150 mM to 20 mM. The current/voltage relationships are summarized in FIG. 10E. The successfully patched cells had whole cell properties that resembled those of wild-type CFTR in epithelial cells (Welsh et al. (1995), Cystic Fibrosis in *THE METABOLIC BASIS OF INHERITED DISEASE* (7th ed.) (Scriver, Beaudet, Sly and Valle, eds.) pp. 3799–3876, McGraw-Hill, New York; Riordan, J. R. (1993), *Annu. Rev. Physiol.* 55: 609–630).

It is highly unlikely that Ca$^{++}$-activated Cl$^-$ was recorded in these experiments because of the presence of 10 mM intracellular EGTA and 100 M extracellular Cd$^{++}$. Under these experimental conditions, 100 pM UTP plus 1 pM ionomycin failed to activate whole cell currents. Special attention was paid to detect possible contribution of the outwardly rectifying Cl$^-$ channel (ORCC) to the whole cell currents. Because of a possible upregulatory role of CFTR, ORCC can be activated in normal but not in CF airway epithelial cells (Hwang et al. (1989), supra.; Li et al. (1988), *Nature* 331: 358–360; Morris and Frizzel (1993); *Am. J. Physiol.*; Schwiebert et al. (1994), *Am. J. Physiol.*). Any involvement of ORCC may provide evidence that DSG restored CFTR function which in return upregulated ORCC. However, several laboratories found that cAMP-stimulated whole cell currents had properties most consistent with activation of CFTR and ORCC did not contribute to cAMP-activated whole cell currents (Bear and Reyes (1992), *Am. J. Physiol.*; Gray et al. (1993); Haws et al. (1992); Wagner et al. (1991), *Nature*; Cliff and Frizzel (1990), *Proc. Natl. Acad. Sci., USA*).

In the whole cell patch studies described herein, there is evidence suggesting that the contribution of ORCC to the whole cell currents in these experiments was minimal, if any. Firstly, all experiments were performed at room temperature. ORCC is rapidly inactivated at room temperature and the remaining current is CFTR (Schwiebert et al., supra) . Secondly, recombinant human CFTR was transduced into CF IBE-1 cells using an adenovirus vector expressing CFTR (Jiang et al. (1996), *Am. J. Physiol.* L527-L537). Whole cell currents recorded in CF IBE-1 cells treated with DSG were almost identical to that recorded in transduced CF IBE-1 cells. Finally, the whole cell currents were markedly (92±4%, n=4) reduced by 200 μM of extracellular DPC which has been shown to specifically inhibit CFTR but not ORCC (Cliff and Frizzel, supra.; Schwiebert et al., supra.)

Although the invention has been described with reference to the disclosed embodiments, those of skill in the art will understand that, using no more than routine experimentation, various modifications can be made without departing from the spirit of the invention. Such equivalents are intended to be encompassed within the scope of the following claims.

What is claimed is:

1. A method for treating defective chloride ion transport in a subject having cystic fibrosis said method comprising:
    administering to said subject a composition
    comprising deoxyspergualin and/or analogs thereof.
2. The method of claim 1 wherein said composition further comprises a pharmaceutically acceptable carrier or diluent.
3. A method for generating chloride channels in a cystic fibrosis (CF)-associated cell, the method comprising:
    contacting said cell with a composition comprising deoxyspergualin and/or analogs thereof.
4. The method of claim 3 wherein the CF-associated cell is an epithelial cell.
5. The method of claim 4 wherein the epithelial cell is an airway epithelial cell.
6. The method of claim 3 wherein said composition further comprises a pharmaceutically acceptable carrier or diluent.

* * * * *